US010730037B2

(12) United States Patent
Miyazawa et al.

(10) Patent No.: US 10,730,037 B2
(45) Date of Patent: Aug. 4, 2020

(54) COMPOUND AND METHOD FOR MANUFACTURING ORGANIC MATERIAL

(71) Applicant: TOYO GOSEI CO., LTD., Chiba (JP)

(72) Inventors: Takashi Miyazawa, Chiba (JP); Ken-ichi Sakaguchi, Chiba (JP)

(73) Assignee: TOYO GOSEI CO., LTD., Chiba (JP)

( * ) Notice: Subject to any disclaimer, the term of this patent is extended or adjusted under 35 U.S.C. 154(b) by 144 days.

(21) Appl. No.: 15/780,396

(22) PCT Filed: Dec. 26, 2016

(86) PCT No.: PCT/JP2016/088793
§ 371 (c)(1),
(2) Date: May 31, 2018

(87) PCT Pub. No.: WO2017/111176
PCT Pub. Date: Jun. 29, 2017

(65) Prior Publication Data
US 2018/0353946 A1 Dec. 13, 2018

(30) Foreign Application Priority Data

Dec. 25, 2015 (JP) .................................. 2015-255310

(51) Int. Cl.
*B01J 31/06* (2006.01)
*C07B 53/00* (2006.01)
(Continued)

(52) U.S. Cl.
CPC .............. *B01J 31/06* (2013.01); *B01J 31/02* (2013.01); *B01J 31/0239* (2013.01); *B01J 38/00* (2013.01);
(Continued)

(58) Field of Classification Search
CPC ................................ B01J 31/061; B01J 20/29
See application file for complete search history.

(56) References Cited

U.S. PATENT DOCUMENTS 4,767,873 A * 8/1988 Katz ....................... C07C 13/62
556/42
5,847,190 A 12/1998 Paulus et al.
(Continued)

FOREIGN PATENT DOCUMENTS

CN  1170714 A   1/1998
EP  0 864 577 A2  9/1998
(Continued)

OTHER PUBLICATIONS

PL-215470-B1 (Dec. 31, 2013); machine translation. (Year: 2013).*
(Continued)

*Primary Examiner* — Rip A Lee
(74) *Attorney, Agent, or Firm* — Maier & Maier, PLLC

(57) ABSTRACT

Synthesis of organic compounds that has chirality is an important technique in the fields of pharmaceuticals, agrichemicals, health foods and the like. However, raw materials of a catalyst used for the synthesis of such compounds are expensive, and the synthesis needs many steps, so that it is difficult to reduce the cost. Linking a catalyst center to a polymer chain or a resin through an organic group enables to use the catalyst repeatedly and produce a chiral compound at low cost.

17 Claims, 12 Drawing Sheets

(51) Int. Cl.

| | |
|---|---|
| C07C 249/02 | (2006.01) |
| C08F 212/14 | (2006.01) |
| C07D 317/28 | (2006.01) |
| B01J 31/02 | (2006.01) |
| C07D 401/06 | (2006.01) |
| C07D 519/00 | (2006.01) |
| B01J 38/00 | (2006.01) |
| C07D 223/14 | (2006.01) |
| C07B 61/00 | (2006.01) |
| C08F 212/36 | (2006.01) |
| C08F 8/00 | (2006.01) |
| C07D 471/10 | (2006.01) |
| C07D 487/10 | (2006.01) |
| C07C 251/24 | (2006.01) |

(52) U.S. Cl.
CPC ............. *C07B 53/00* (2013.01); *C07B 61/00* (2013.01); *C07C 249/02* (2013.01); *C07C 251/24* (2013.01); *C07D 223/14* (2013.01); *C07D 317/28* (2013.01); *C07D 401/06* (2013.01); *C07D 471/10* (2013.01); *C07D 487/10* (2013.01); *C07D 519/00* (2013.01); *C08F 8/00* (2013.01); *C08F 212/14* (2013.01); *C08F 212/36* (2013.01); *B01J 31/061* (2013.01); *B01J 2231/42* (2013.01); *B01J 2231/46* (2013.01); *B01J 2531/0261* (2013.01); *B01J 2531/0263* (2013.01); *B01J 2531/0266* (2013.01)

(56) References Cited

U.S. PATENT DOCUMENTS

| | | | |
|---|---|---|---|
| 6,143,834 A | 11/2000 | Tamao et al. | |
| 6,248,848 B1 | 6/2001 | Tamao et al. | |
| 6,369,257 B1 | 4/2002 | Bunel et al. | |
| 7,566,779 B2* | 7/2009 | Maruoka | C07C 251/24 540/543 |
| 7,709,678 B2* | 5/2010 | Koshima | B01J 31/0239 560/155 |
| 8,367,820 B2* | 2/2013 | Maruoka | C07B 53/00 540/543 |
| 8,962,898 B2* | 2/2015 | Maruoka | C07B 53/00 570/130 |
| 9,018,394 B2* | 4/2015 | Ishihara | C07D 209/12 548/312.1 |
| 9,687,833 B2* | 6/2017 | Kanaya | C07C 205/48 |
| 2010/0029935 A1 | 2/2010 | Maruoka et al. | |
| 2013/0338292 A1* | 12/2013 | Fujita | C04B 35/62839 524/430 |

FOREIGN PATENT DOCUMENTS

| | | | | |
|---|---|---|---|---|
| JP | 2009-235393 A | | 10/2009 | |
| JP | 2009235393 A | * | 10/2009 | ............ C08F 212/14 |
| JP | 2012-240959 A | | 12/2012 | |
| PL | 215470 B1 | * | 12/2013 | ............ C07D 233/60 |
| WO | WO-2014196542 A1 | * | 12/2014 | ............ C07C 201/16 |

OTHER PUBLICATIONS

Kobayashi, N.; Iwai, K. J. Am. Chem. Soc. 1978, 100, 7071-7072. (Year: 1978).*

Frechet, J.M.J.; Kelly, J.; Sherrington, D.C. Polymer, 1984, 25, 1491-1498. (Year: 1984).*

Partial Search Report dated Oct. 16, 2018 in corresponding European Application No. 16879060.8; 13 pages.

Bayston et al., "Preparation and Use of a Polymer Supported BINAP Hydrogenation Catalyst", Journal of Organic Chemistry, vol. 63, No. 9, 1998, pp. 3137-3140.

International Search Report dated Feb. 28, 2017 of corresponding International application No. PCT/JP2016/088793; 6 pgs.

Maurizio Benaglia et al., "Polymer-Supported Organic Catalysts", Chemical Reviews, 2003, vol. 103, No. 9, p. 3401-3429; 29 pgs.

J. M. J. Frechet et al., "Some novel polymer-supported optically active phase transfer catalysts: 1. Synthesis", Polymer, 1984, vol. 25, p. 1491-1498; 8 pgs.

J. Kelly et al., "Some novel polymer-supported optically active phase transfer catalysts: 2. Use in displacement"\, reduction, epoxidation and addition reactions, Polymer, 1984, vol. 25, p. 1499-1504; 6 pgs.

Norio Kobayashi, "Asymmetric Reactions Catalyzed by Chiral Synthetic Polymers", Journal of Synthetic Organic Chemistry, Japan, 1981, vol. 39, No. 3, p. 181 to 191; 11 pgs. with English abstract.

Naoki Haraguchi, "Synthesis of Polymer-Supported Chiral Catalyst and Its Application to Asymmetric Reactions", Japanese Journal of Polymer Science and Technology, 2010, vol. 67, No. 8, p. 447-464; 18 pgs. with English abstract.

Chinese Office Action dated Apr. 8, 2020, in connection with corresponding CN Application No. 201680074944.0 (15 pgs., including machine-generated English translation).

\* cited by examiner

COMPOUND AND METHOD FOR MANUFACTURING ORGANIC MATERIAL

TECHNICAL FIELD

Some aspects of the present invention relate to a polymer or a resin having chirality, and a synthesis of an organic compound using it as a catalyst.

BACKGROUND ART

A synthesis of an organic compound having chirality is an important technique in the fields of pharmaceuticals, agrichemicals, health foods and the like. However, a raw material of a catalyst used for the synthesis is expensive, and the synthesis needs many steps, so that it is difficult to reduce the cost.

Some embodiments of the present invention provide a technique that enable to produce a compound having chirality at low cost.

CITATION LIST

Patent Literature

Patent Literature 1: JP2012-240959

SUMMARY OF INVENTION

A compound according to an embodiment of the present invention comprises: a plurality of first portions; a second portion; and a linker connecting each of the plurality of first portions with the second portion and having at least a covalent bond, wherein each of the plurality of first portions has chirality, and the compound has no coordinating nitrogen atom in a portion other than the linker.

Typical schematic structures which the above compound has illustrated in FIGS. 1 and 2.

In the structure illustrated in FIG. 1, each of the plurality of first portions having chirality is bonded to the second portion through the linker. The second portion may constitute a main chain of a polymer, and the structure illustrated in FIG. 1 may further crosslink through a crosslinker.

In the structure illustrated in FIG. 2, each of the plurality of first portions having chirality bonds to the second portion through the linker. Each of the plurality of first portions, the linker and the second portion are one repeating unit, and a plurality of the repeating units links to constitute the main chain. That is, in the structure illustrated in FIG. 2, a portion having chirality is a part of the main chain.

In the compound, as described later, the compound preferably has no coordinating nitrogen atom other than the linker since a stereoselectivity of an asymmetric reaction using the compound as a catalyst tends to decrease. This is because a coordinating ability of the coordinating nitrogen atom may decrease a steric influence due to the chirality which each of the plurality of first portions has in the asymmetric reaction.

The coordinating nitrogen atom in the embodiment of the present invention indicates a nitrogen atom having a high electron density of a lone pair on the nitrogen atom. Specifically, the coordinating nitrogen atom refers to a nitrogen atom bonding to two carbon atoms, and not bonding to an atom other than a carbon atom and a hydrogen atom within three bonds including bonds between the nitrogen atom and the carbon atoms. Examples include a nitrogen atom contained in pyridine, quinoline and the like.

When a structure has a hetero atom of higher electronegativity than a carbon atom, such as an oxygen atom, and the hetero atom is neither a carbon atom nor a hydrogen atom, within two bonds including the nitrogen atom such as an amide group, the electron density of the lone pair on the nitrogen atom decreases and the coordinating ability of the nitrogen atom itself may decrease due to an influence of the oxygen atom. Therefore, in the above embodiment of the present invention, such nitrogen atom is not regarded as the coordinating nitrogen atom.

When a structure has a hetero atom of a lower-electronegativity element than a carbon atom within three bonds including the nitrogen atom, a level of an anti-bonding orbital of a bond containing the hetero atom may decrease. The electron density of the lone pair on the nitrogen atom decreases due to the stabilized anti-bonding orbital, and the coordinating ability of the nitrogen atom itself may decrease. Therefore, in the above embodiment of the present invention, such nitrogen atom is not regarded as the coordinating nitrogen atom.

A compound according to another embodiment of the present invention comprises: a plurality of first portions; a second portion; and a linker connecting each of the plurality of first portions with the second portion and having at least a covalent bond, wherein each of the plurality of first portions has chirality, and the chirality is induced by any one selected from the group consisting of an asymmetric atom, an axial chirality, a planar chirality and a helix.

When the chirality is induced by the asymmetric atom, each of the plurality of first portions has a first atom bonding directly to the asymmetric atom, and the linker bonds directly to the first atom.

When the chirality is induced by the axial asymmetry, each of the plurality of first portions has an axially chiral substituent to be the axial chirality, the linker bonds directly to: a second atom contained in a cyclic structure sharing a plurality of atoms with constituent atoms constituting the axially chiral substituent; or a third atom contained in the axially chiral substituent, and a bond between: a fourth atom; and the second atom or the third atom is rotatable, the fourth atom being contained in the linker and bonding directly to the second atom or the third atom.

When the chirality is induced by the planar chirality, the compound has a planar-chiral substituent to be the planar chirality, the linker bonds directly to a fifth atom contained in the planar-chiral substituent, and a bond between a sixth atom and the fifth atom is rotatable, the sixth atom being contained in the linker and bonding directly to the planar-chiral substituent.

When the chirality is induced by the helix, the compound has a helical substituent to be the helix, the linker bonds directly to the seventh atom contained in the helical substituent, and a bond between an eighth atom and the seventh atom is rotatable, the eighth atom bonding directly to the helical substituent.

The axially chiral substituent, the planar-chiral substituent and the helical substituent has no freely rotatable bond.

In the above compound, it is preferred that the compound is an organic salt including a cation portion and an anion portion, the compound further includes a third portion, the third portion is the anion portion, and the cation portion includes the plurality of first portions, the second portion and the linker.

In any one of the above compounds, each of the plurality of first portions preferably has a substituent having the asymmetric atom, the axial chirality, the planar chirality or the helical structure.

FIG. 3 illustrates an example of a compound containing the asymmetric atom according to an embodiment of the present invention. The example of the compound illustrated in FIG. 3 has a proline skeleton, the asymmetric atom is a carbon atom contained in a pyrrolidine ring, and the carbon atom bonds directly to a carboxyl group and a nitrogen atom in the pyrrolidine ring.

Herein, the first portion in the compound according to an embodiment of the present invention is a portion having the carbon atom and four atoms bonding directly to the carbon atom, the four atoms making the carbon atom to be asymmetric. The linker is a portion connecting the first portion and the second portion at the shortest, and the second portion includes a bond of a plurality of carbon atoms. The linker is a portion from a carbon atom contained in the pyrrolidine ring to an ester group, the carbon atom bonding to the nitrogen atom bonding directly to the asymmetric carbon atom, and the ester group containing a carbon atom bonding directly to a carbon atom contained in the second portion.

In the example of the compound illustrated in FIG. 3, the second portion is formed by connecting a plurality of carbon atoms, but the second portion of the compound according to an embodiment of the present invention typically has constituent atoms which may be a different element, and the constituent atoms may bond with a single bond or a multiple bond. A number of the constituent atoms is preferably 20 or more.

Note that, a polymer compound to which the proline skeleton portion is bonded illustrated in FIG. 3 can be used as a catalyst containing no metal atoms for an aldol reaction.

In the compound exemplified in FIG. 3, the first atom is, for example, a nitrogen atom contained in the pyrrolidine ring skeleton.

FIG. 4 illustrates an example of a compound according to an embodiment of the present invention containing a substituent inducing the axial chirality. The compound illustrated in FIG. 4 is an organic salt having a binaphthyl group as the substituent inducing the axial chirality. In the compound, the first portion refers to a portion containing an axially chiral substituent and a cyclic structure sharing at least two atoms constituting the axially chiral substituent. The cyclic structure is contained in the first portion having chirality so that a conformation of the axially chiral substituent may be reflected in the cyclic structure containing at least the two atoms constituting the axially chiral substituent. As the first portion of the compound according to some embodiments of the present invention, it is preferred that the conformation is substantially fixed or a freely rotatable bond is not contained, such as the first portion of the compound illustrated in FIG. 4.

Setting a number of atoms constituting the cyclic structure sharing a plurality of atoms in atoms contained in the axially chiral substituent to be 10 or less contributes to fixation of the conformation. By further setting the number to be 8 or less, the conformation is more fixed. When a compound having the axially chiral substituent and the cyclic structure having a plurality of atoms constituting the axially chiral substituent, as illustrated in FIG. 4, is used as a catalyst for an asymmetric reaction, it is particularly preferred that the cyclic structure is constituted of 7 or less atoms so that high optical yield tend to be obtained by restricting of change in the conformation or restriction of free rotation of a bond.

In the compound illustrated in FIG. 4, the first portion specifically refers to a portion composed, in addition to the binaphthyl group, a seven-membered ring which is composed of a carbon atom at 1-position of the binaphthyl skeleton, a carbon atom at 1'-position of the binaphthyl skeleton, a carbon atom at 2-position of the binaphthyl group, a carbon atom at 2'-position of the binaphthyl group, a methylene group bonding to the carbon atom at 2-position of the binaphthyl skeleton, a methylene group bonding to the carbon atom at 2'-position of the binaphthyl skeleton and a nitrogen atom which is a cation center of the organic salt. The linker refers to a portion from a carbon atom bonding directly to the nitrogen atom to an oxygen atom bonding directly to a carbon atom of the second portion. Note that the second atom and the fourth atom are contained in the seven-membered ring, and respectively correspond to the nitrogen atom of the cation center of the ammonium salt and a carbon atom of the linker bonding directly to the nitrogen atom.

Since the compound exemplified in FIG. 4 is an organic salt, the compound contains a bromide ion as a counter ion. In a typical example of a compound according to an embodiment of the present invention, a portion such as the bromide ion, forming no covalent bond with the first portion, the linker or the second portion is regarded as the third portion. In a typical example of a compound according to an embodiment of the present invention, the substituent R is an organic group which may have a substituent.

FIG. 5 illustrates an example of a compound according to an embodiment of the present invention comprising a substituent inducing the axial chirality. Like the compound illustrated in FIG. 4, the compound is an organic salt having a binaphthyl group as a substituent inducing the axial chirality. In the compound, the first portion refers to a portion including an axially chiral substituent and a cyclic structure sharing at least two atoms with constituent atoms constituting the axially chiral substituent. Specifically, the first portion refers to, in addition to the binaphthyl group, a portion composed of a seven-membered ring including a carbon atom at 1-position of the binaphthyl skeleton, a carbon atom at 1'-position of the binaphthyl skeleton, a carbon atom at 2-position of the binaphthyl skeleton, a carbon atom at 2'-position of the binaphthyl skeleton, a methylene group bonding to the carbon atom at 2-position of the binaphthyl skeleton, a methylene group bonding to the carbon atom at 2'-position of the binaphthyl skeleton and a nitrogen atom of the cation center of the organic salt.

The linker refers to a portion from an oxygen atom bonding directly to the carbon atom at 3-position of the binaphthyl skeleton to an oxygen atom bonding directly to a carbon atom of the second portion. The oxygen atom bonding directly to the carbon atom at 3-position of the binaphthyl skeleton is contained in the linker so that a bond between the carbon atom at 3-position of the binaphthyl skeleton and the oxygen atom bonding directly to the carbon atom is freely rotatable with almost no effect of a conformation of the binaphthyl group as the axially chiral substituent. The third atom corresponds to the carbon atom at 3-position of the binaphthyl skeleton, and the fourth atom corresponds to the oxygen atom of the linker bonding directly to the carbon atom at 3-position.

Since the compound exemplified in FIG. 5 is an organic salt, the compound contains a bromide ion as a counter ion. In a typical example of a compound according to an embodiment of the present invention, a portion such as the bromide ion, forming no covalent bond with the first portion, the linker, or the second portion, is regarded as the third portion. In a typical example of a compound according to an embodiment of the present invention, the substituents $R^1$ and $R^2$ are organic groups which may be same or different from each other and may have a substituent.

FIG. 6 illustrates an example of a compound according to an embodiment of the present invention containing a plurality of substituents inducing the axial chirality. This compound includes: two binaphthyl groups of the axially chiral substituent; and two seven-membered rings sharing a plurality of atoms in constituent atoms constituting each of the two binaphthyl groups and having a carbon atom at 1-position of the binaphthyl skeleton, a carbon atom at 1'-position of the binaphthyl skeleton, a carbon atom at 2-position of the binaphthyl skeleton, a carbon atom at 2'-position of the binaphthyl skeleton, a methylene group bonding to 2-carbon atom of the binaphthyl skeleton, a methylene group bonding to 2'-carbon atom of the binaphthyl skeleton and a nitrogen atom of the cation center of the organic salt. A conformation is substantially fixed by the seven-membered ring structure. A portion in which the conformation is substantially fixed in this way, such that the nitrogen atom is shared by two seven-membered ring structures, is defined as the first portion in the compound according to some embodiments of the present invention. In addition, this first portion also does not include a freely rotatable bond.

In the compounds illustrated in FIG. 6, the linker refers to a portion from an oxygen atom bonding directly to a carbon atom at 6-position of the binaphthyl skeleton to a carbon atom of a benzene ring bonding directly to a carbon atom constituting the second portion. The oxygen atom bonding directly to the carbon atom at 6-position of the binaphthyl skeleton is contained in the linker so that a bond between the carbon atom at 6-position of the binaphthyl skeleton and the oxygen atom bonding directly to the carbon atom is freely rotatable with almost no effect of the conformation of the binaphthyl group as the axially chiral substituent. The third atom corresponds to the carbon atom at 6-position of the binaphthyl skeleton, and the fourth atom corresponds to the oxygen atom contained in the linker bonding directly to the carbon atom.

Since the compound exemplified in FIG. 6 is an organic salt, the compound contains a bromide ion as a counter ion. In a typical example of a compound according to an embodiment of the present invention, a portion such as the bromide ion, forming no covalent bond with the first portion, the linker, or the second portion, is regarded as the third portion. In a typical example of a compound according to an embodiment of the present invention, the substituent R is an organic group which may have a substituent.

FIG. 7 illustrates an example of a compound according to an embodiment of the present invention containing: a biphenyl group of the axially chiral substituent; and a cyclic structure sharing a plurality of atoms in constituent atoms constituting the biphenyl group and the cyclic structure having an oxygen atom of ortho position to a bond formed between two benzene rings of the biphenyl group. In the compound, the biphenyl group and the cyclic structure are defined as the first portion, and the linker is a portion from an oxygen atom bonding directly to the cyclic structure to an oxygen atom bonding directly to the second portion constituting the main chain.

The fourth atom corresponds to the oxygen atom bonding directly to the cyclic structure, and the second atom corresponds to the carbon atom contained in the cyclic structure bonding directly to the oxygen atom.

The substituents $R^1$ and $R^2$ of the compounds exemplified in FIG. 7 are organic groups which may be same or different from each other and may have a substituent, but when these substituents do not contribute to a steric hindrance which makes the biphenyl group to be axially chiral and the cyclic structure contributes to the steric hindrance which makes the biphenyl group to be axially chiral, it is interpreted that the substituents $R^1$ and $R^2$ are not contained in the first portion.

FIG. 8 illustrates an example of a compound according to an embodiment of the present invention including the planar-chiral substituent. The compound illustrated in FIG. 8 has a cyclophane structure as the planar-chiral substituent and has optical activity because its conformation is fixed. Therefore, a portion composed of a six-membered ring having a nitrogen atom, the portion being a unit inducing the optical activity, and a moiety having 10 methylene chains connecting two opposed carbon atoms of the six-membered ring are defined as the first portion.

The linker is defined as a portion from a carbon atom of an amide group bonding directly to the six-membered ring to a carbon atom bonding directly to a silicon atom of the second portion of the main chain. In this compound, the fifth atom corresponds to a carbon atom contained in the six-membered ring containing the nitrogen atom and the carbon atom bonding directly to an amide group, and the sixth atom corresponds to a carbon atom of the amide group. A bond between these two carbon atoms is freely rotatable. In other word, in this compound, a conformation of the amide group bonding directly to the cyclophane structure, which is the planar-chiral group, is not substantially fixed to the cyclophane structure.

The second portion of the compound illustrated in FIG. 8 has a branched siloxane structure, but in a compound according to some embodiments of the present invention, the second portion may have a branched structure or a crosslinked structure.

FIG. 9 illustrates an example of a compound including a helical structure according to an embodiment of the present invention. The compound has a helicene skeleton having five benzene rings as the helical structure. The helicene skeleton has two organic groups, and a phosphorus atom coordinating to a palladium atom bonds to the helicene skeleton. In this compound, a portion containing: the helicene skeleton having the helical structure; the palladium atom; and a phosphorus atom having two organic groups and coordinating to the palladium atom; is defined as the first portion. That is, a portion where a conformation is fixed to the helical structure is defined as the first portion.

When the first portion inducing optical activity is included in the main chain structure like the compound illustrated in FIG. 9, an atom bonding to the first portion is defined as the linker, and a portion bonding to the atom contained in the linker is defined as the second portion. The seventh atom corresponds to two carbon atoms in carbon atoms constituting the helicene skeleton, the two carbon atoms bonding to an oxygen atom as the linker. The eighth atom corresponds to the oxygen atom bonding directly to the two carbon atoms.

When the second portion has a cyclic structure like the compound exemplified in FIG. 9, a number of atoms does not correspond to a chain length. Thus, to compare with a compound having no cyclic structure in the second portion, in the part of the cyclic structure, only a series of bonds on one side is counted. Specifically, referring to FIG. 9 as an example, the number of atoms among: the oxygen atom of the linker; a benzene ring bonding to the oxygen atom; and an oxygen atom bonding directly to the benzene ring in the second portion is considered as 4.

Note that for a compound having an optically active moiety in the main chain, it may be difficult to obtain a high molecular weight compound in general due to a steric hindrance or the like. Therefore, in some cases, it may be advantageous that the first portion having optical activity bonds to the main chain through the linker as the structure illustrated in FIG. 1.

FIG. 10 illustrates an example of a compound having two asymmetric centers according to an embodiment of the present invention. A portion containing four atoms which make each of the two asymmetric centers to be asymmetric is defined as the first portion. A portion from a nitrogen atom being one of the two cation centers in the compound and bonding directly to the first portion to an oxygen atom bonding directly to the second portion is defined as the linker.

In a compound according to some embodiments of the present invention, examples of a structural unit having the axial chirality include an allenyl group which may have a substituent, in addition to the biphenyl group and the binaphthyl group including a bond of two aromatic groups which may have a substituent.

In a compound according to some embodiments of the present invention, examples of a structural unit having the planar chirality include a trans-cyclooctene structure and a ferrocenyl substituent which may have a substituent, in addition to the cyclophane structure.

In a compound according to some embodiments of the present invention, examples of the structural unit having a helical structure include a protein and an nucleic acid, in addition to the compound having the helicene skeleton described above.

In any one of the above compounds, each of the plurality of first portions preferably has a substituent having the axial chirality.

In any one of the above compounds, it is preferred that each of the plurality of first portions has a binaphthyl group inducing chirality by the axial chirality and a nitrogen atom, and a part of the binaphthyl group and the nitrogen atom constitute at least one part of the cyclic structure.

A compound according to an embodiment of the present invention comprises: a plurality of first portions; a second portion; a third portion; and a linker connecting each of the plurality of first portions with the second portion and having at least one covalent bond, the compound is an organic salt, and the plurality of first portions has chirality. In the compound, each of the plurality of first portions having chirality bonds to the second portion through the linker so that leakage of the plurality of first portions due to salt exchange or the like is suppressed and deterioration of the chirality of the compound is suppressed when a salt is added for the reaction using the compound as a catalyst or when a salt forms as a result of a reaction.

In any one of the compounds, the third portion preferably does not form a covalent bond with the plurality of first portions, the second portion, or the linker. In a compound according to some embodiments of the present invention, examples of the third portion include anion species such as a hydroxide ion, a halide ion such as an iodide ion, a bromide ion, a chloride ion and a fluoride ion, a tetrafluoroborate ion, a hexafluorophosphate ion, a nitrate ion, a sulfate ion, a cyanide ion, a phosphate ion, a thiocyanate ion and a perchlorate ion.

In any one of the above compounds, it is preferred that the organic salt is composed of a cation portion and an anion portion, the third portion is the anion portion, and the cation portion includes the plurality of first portions, the second portion and the linker.

In any one of the above compounds, the compound preferably has no coordinating nitrogen atom in a portion other than the linker.

In any one of the above compounds, the compound preferably has no coordinating nitrogen atom in a portion other than the linker, since stereoselectivity of an asymmetric reaction using the compound as a catalyst tends to decrease as described later. This is because a steric influence due to chirality which each of the plurality of first portions has in the asymmetric reaction may be deteriorated by a coordination ability of the coordinating nitrogen atom.

In a compound according to some embodiments of the present invention, the coordinating nitrogen atom refers to a nitrogen atom having a high electron density of a lone pair on the nitrogen atom. Specifically, the nitrogen atom refers to a nitrogen atom bonding to two carbon atoms, and not bonding to an atom other than a carbon atom and a hydrogen atom within the three bonds including bonds between the nitrogen atom and the carbon atoms. An example is a nitrogen atom contained in pyridine, quinoline and the like.

When a structure has a hetero atom of higher electronegativity than a carbon atom, such as an oxygen atom, (that is neither a carbon atom nor a hydrogen atom) within two bonds including the nitrogen atom such as an amide group, the electron density of the lone pair on the nitrogen atom decreases and the coordinating ability of the nitrogen atom itself may decrease due to an influence of the oxygen atom. Therefore, in the above embodiment of the present invention, such nitrogen atom is not regarded as a coordinating nitrogen atom.

When a structure has a hetero atom of a lower-electronegativity element than a carbon atom within three bonds including the nitrogen atom, a level of an anti-bonding orbital of a bond containing the hetero atom may decrease. The electron density of the lone pair on the nitrogen atom decreases due to the stabilized anti-bonding orbital, and the coordinating ability of the nitrogen atom itself may decrease. Therefore, in the above embodiment of the present invention, such nitrogen atom is not regarded as a coordinating nitrogen atom.

In any one of the above compounds, it is preferred that the compound is an organic salt including a cation portion and an anion portion, the third portion is the anion portion, and the cation portion includes the plurality of first portions, the second portion and the linker.

In any one of the above compounds, each of the plurality of first portions preferably has a substituent having an asymmetric carbon atom, an axial chirality, a planar chirality or a helical structure.

Examples of a structural unit having the axial chirality include an allenyl group which may have a substituent, and the biphenyl group and the binaphthyl group including a direct bond of two aromatic groups which may have a substituent.

Examples of a structural unit having the planar chirality include a cyclophane structure, a trans-cyclooctene structure, and a ferrocenyl substituent which may have a substituent.

Examples of a structural unit having the helical structure include a helical structure in which a plurality of aromatic rings or heterocyclic rings bond.

Among the asymmetric carbon atom, the axial chirality, the planar chirality or the helical structure, the axial chirality, the planar chirality or the helical structure is preferable as a method for inducing chirality. This is because when a compound according to some embodiments of the present invention is used as a catalyst for an asymmetric reaction, the axial chirality, the planar chirality or the helical structure can control an approach of a substrate to the catalyst in a wider space so that the optical yield may tend to be improved.

In any one of the above compounds, it is particularly preferred that each of the plurality of first portions has a substituent having the axial chirality.

In any one of the above compounds, each of the plurality of first portions has a binaphthyl group inducing chirality by the axial chirality, and a nitrogen atom. Apart of the binaphthyl group and the nitrogen atom preferably constitute at least one part of the cyclic structure.

It is preferred that a compound according to an embodiment of the present invention comprises a plurality of first portions; a second portion; a third portion; and a linker connecting each of the plurality of first portions with the second portion and having at least one covalent bond, the compound is an organic salt, the plurality of first portions has chiralilty, and a coordinating nitrogen atom is not present within 6 bonds from a bond having an atom which is a cation or an anion center of the organic salt.

In this compound, each of the plurality of first portions preferably has chirality. In this compound, it is preferred that the coordinating nitrogen atom does not present within 5 or 4 bonds from an asymmetric center of the chirality.

In the compound, the coordinating nitrogen atom preferably does not present within 6 bonds from a bond having an atom of the cation or an anion center of the organic salt because a stereoselectivity of an asymmetric reaction using the compound as a catalyst tends to decrease, as described later. This is because the steric influence due to chirality which each of the plurality of first portions has in the asymmetric reaction may be deteriorated by a coordinating ability of the coordinating nitrogen atom.

In the compound, the coordinating nitrogen atom preferably does not present within 5 or 4 bonds from a bond having an atom of the asymmetric center because a stereoselectivity of an asymmetric reaction using the compound as a catalyst tend to decrease, as described later. This is because the steric influence due to chirality which each of the plurality of first portions has in the asymmetric reaction may be deteriorated by the coordinating ability of the coordinating nitrogen atom.

The coordinating nitrogen atom in the compound refers to a nitrogen atom having a high electron density of a lone pair on the nitrogen atom. Specifically, the coordinating nitrogen atom refers to a nitrogen atom bonding to two carbon atoms, and not bonding to an atom other than a carbon atom and a hydrogen atom within the three bonds including bonds between the nitrogen atom and the carbon atoms. Examples include a nitrogen atom contained in pyridine, quinoline and the like.

When a structure has a hetero atom of higher electronegativity than a carbon atom, such as an oxygen atom, and the hetero atom is neither a carbon atom nor a hydrogen atom within two bonds including the nitrogen atom such as an amide group, the electron density of the lone pair on the nitrogen atom decreases and the coordinating ability of the nitrogen atom itself may decrease due to an influence of the oxygen atom. Therefore, in the above embodiment of the present invention, such nitrogen atom is not regarded as a coordinating nitrogen atom.

When a structure has a hetero atom of a lower-electronegativity element than a carbon atom within three bonds including the nitrogen atom, a level of an anti-bonding orbital of a bond containing the hetero atom may decrease. The electron density of the lone pair on the nitrogen atom decreases due to the stabilized anti-bonding orbital, and the coordinating ability of the nitrogen atom itself may decrease. Therefore, in the above embodiment of the present invention, such nitrogen atom is not regarded as a coordinating nitrogen atom.

In such compound, each of the plurality of first portions having chirality bonds to the second portion through the linker so that leakage of the plurality of first portions due to salt exchange or the like is suppressed and deterioration of the chirality of the compound is suppressed when a salt is added for a reaction using the compound as a catalyst or when a salt forms as a result of a reaction.

In any one of the above compounds, the second portion preferably includes a bond of 20 or more constituent atoms.

In any one of the above compounds, the second portion preferably includes a bond of 30 or more constituent atoms.

In any one of the above compounds, the second portion preferably includes a bond of 50 or more constituent atoms.

In any one of the above compounds, the second portion preferably includes a bond of 100 or more constituent atoms.

By increasing the number of constituent atoms of the second portion, insolubility to a solvent is improved. According to such feature, for example, when the above compound is used as a catalyst or the like in an organic reaction, the compound can be recovered by a simple operation such as filtration.

In any one of the above compounds, the constituent atom is preferably a carbon atom. Since a bond of a carbon atom with general hetero atoms such as a nitrogen atom and an oxygen atom, a hydrogen atom or a carbon atom are generally chemically stable, the compound can be applied to various functional materials.

In any one of the above compounds, the compound preferably does not contain a metal atom in the structure. The metal atom may give a bad effect to a living body and may cause degradation of performance of a device, so that, it has been required that the metal atom is not contained. Therefore, such feature may be preferred as the compound.

In any one of the above compounds, it is preferred that either the cation portion and the anion portion of the organic salt at least does not contain ionic bonds, or the cation and anion portion are formed only by a covalent bond. This enables, for example, to suppress deterioration due to salt exchange or the like in the presence of a solvent or the like.

In any one of the above compounds, it is preferred that each of the plurality of first portions contains a binaphthyl group inducing chirality by the axial chirality and a nitrogen atom, and a part of the binaphthyl group and the nitrogen atom constitute at least one part of a cyclic structure. A number of ring members is preferably 5 to 10. Particularly, the number of ring members is preferably 6 and 7.

In any one of the above compounds, each of the plurality of first portions preferably contains a cation center of an ammonium salt. Typical examples of the cation center include a nitrogen atom having a positive charge.

In any one of the above compounds, the linker preferably connects the cation center with the second portion.

In any one of the above compounds, it is preferred that the nitrogen atom bonds to a carbon atom at 2-position of the binaphthyl group and a carbon atom at 2'-position of the binaphthyl group through a first methylene group and a second methylene group, respectively, the nitrogen atom further bonds to a first and second organic groups in addition to the first methylene group and the second methylene group, and the linker has the first organic group.

In any one of the above compounds, the linker preferably has an oxygen atom.

In any one of the above compounds, the linker preferably has the oxygen atom and a hydrocarbon group including a bond of a plurality of carbon atoms.

In any one of the above compounds, the hydrocarbon group preferably includes a bond of 6 or more carbon atoms.

In any one of the above compounds, the second portion preferably has a molecular weight of 8000 or more.

In any one of the above compounds, the second portion preferably has a molecular weight of 8000 or more.

In any one of the above compounds, the second portion preferably has a molecular weight of 10000 or more.

In any one of the above compounds, the second portion preferably has a molecular weight of 15000 or more.

In any one of the above compounds, the second portion preferably has a molecular weight of 20000 or more.

In any one of the above compounds, the second portion preferably has a molecular weight of 25000 or more.

In any one of the above compounds, the second portion preferably has a molecular weight of 30000 or more.

In any one of the above compounds, the second portion preferably has a molecular weight of 30000 or more.

In any one of the above compounds, the second portion preferably has a molecular weight of 40000 or more.

In any one of the above compounds, the second portion preferably has a molecular weight of 50000 or more.

In any one of the above compounds, the second portion preferably has a molecular weight of 60000 or more.

In any one of the above compounds, the second portion preferably has a molecular weight of 70000 or more.

In any one of the above compounds, the second portion preferably has a molecular weight of 80000 or more.

In any one of the above compounds, the second portion preferably has a molecular weight of 100000 or more.

In any one of the above compounds, the second portion preferably has a molecular weight of 150000 or more.

In any one of the above compounds, the second portion preferably has a molecular weight of 200000 or more.

In any one of the above compounds, the second portion preferably has a molecular weight of 300000 or more.

By increasing the molecular weight of the second portion, the insolubility to a solvent is further improved. According to such feature, for example, when any of the above compound is used as a catalyst or the like in an organic reaction, the compound can be recovered by a simple operation such as filtration.

In any one of the above compounds, the second portion preferably has a branched or crosslinked structure. Typical examples of the structure of the second portion include a structure in which the main chains are connected by one or more covalent bonds or a mesh-like structure.

By such structure, the insolubility to the solvent is further improved. According to such feature, for example, when any of the above compounds is used as a catalyst or the like in a reaction, the compound can be recovered by a simple operation such as filtration after the reaction, and the recovered compound can be reused.

In any one of the above compounds, examples of the second portion include: a portion having a carbon atom and an oxygen atom in the main chain such as an alkyl chain, an ether structure, a polyoxyalkylene which may have a substituent or a side chain group; a portion having a carbon atom and a nitrogen atom in the main chain such as a polyethyleneimine which may have a substituent or a side chain group; a portion having an atom of hetero element such as a silicon other than a carbon atom, an oxygen atom and a nitrogen atom in the main chain such as a siloxane which may have a substituent or a side chain group; a portion having a nylon structure in the main chain, where the nylon structure may have a substituent or a side chain group; a portion having a vinylon structure in the main chain, where the vinylon structure may have a substituent or a side chain group; a portion having a polyester structure in the main chain such as a polyethylene terephthalate, where the polyester structure may have a substituent or a side chain group; a portion having an amide bond in the main chain, where the amide bond may have a substituent or a side chain group; a portion having a polyimide structure in the main chain, where the polyamide structure may have a substituent or a side chain group; and a portion having a polysaccharide structure in the main chain, where the polysaccharide structure may have a substituent or a side chain group.

The second portion may contain an aromatic ring or a heterocyclic ring in the main chain. The second portion may further contain a hetero atom such as a sulfur atom, a phosphorus atom or the like in the main chain.

Among the main chain structures of the second portion exemplified above, the portion having an alkyl chain and an ether structure which may have a substituent or a side chain group are preferred. An alkyl chain and an ether bond have large bond energy and are stable, so that it is possible to suppress deterioration when one of the above compounds is used as a catalyst for a reaction.

Moreover, for example, by increasing a polarity of the plurality of first portions, the polarity difference between the plurality of first portions and the second portions increases so that when one of the above compounds is used as a catalyst for a reaction and the reaction proceeds via a polar transition state, the reaction proceeds in a vicinity of the plurality of first portions, each of which has chirality, and it has advantage in inducing chirality.

In order to increase the polarity of the plurality of first portions, for example, the first portion may be an organic salt structure. Examples include a structure having an electron accepting group or an electron donating group such as a nitro group, a cyano group, a hydroxy group and an amino group, the amino group may have a substituent.

In any one of the above compounds, the linker may have: an aryl group; an alkyl chain; an amide bond; an ether bond; a thioether bond; a disulfide bond; an imide bond; a single bond or a double bond between a carbon atom and a nitrogen atom; a bond between a phosphorus atom and a carbon atom; or a bond between a phosphorus atom and an oxygen atom.

In addition to the bonds exemplified above as the bond contained in the linker, the linker may further contain an aryl group.

In any one of the above compounds, it is preferred that the linker contains an aryl group and the aryl group bonds to the second portion. According to such structure, rigidity of the compound increases, insolubility to a solvent is improved, and the compound can be recovered by a simple operation such as filtration even after using the compound as a catalyst of a reaction.

In any one of the above compounds, any of the carbon atoms of the alkyl chain constituting the second portion preferably has a substituent. According to such structure, a fine cavity can form in the compound, and when the compound is used as a catalyst of a reaction, the cavity may be a reaction field. In the compound, when the second portion has an aryl group as the substituent, rigidity increases, insolubility is improved, and the compound can be easily recovered even after using the compound as the catalyst of the reaction.

Any one of the above compounds can be used as a catalyst to induce chirality. Although the catalyst inducing chirality is usually expensive, but as mentioned above, increasing the insolubility of the compound facilitates to recover or reuse the compound by filtration or the like so that a cost for carrying out an asymmetric synthesis reduces.

A method for manufacturing an organic material according to an embodiment of the present invention comprises a first step of proceeding with an organic reaction by using the compound of any one of the above compounds as a catalyst.

The method for manufacturing an organic material preferably further comprises a second step of recovering the compound after the first step. According to such method, when the compound is expensive, the compound can be repeatedly used and an organic material can be manufactured at low cost.

The method for manufacturing an organic material preferably further comprises a third step of reusing the recovered compound in the second step as a catalyst to proceed with an organic reaction.

A method for manufacturing an organic material according to another embodiment of the present invention comprises: a first step of preparing a container or a column filled with the compound according to any one of the above compound; and a second step of proceeding with an organic reaction in the container or the column using the compound as a catalyst. By using the container or the column filled with the catalyst as the method for manufacturing an organic material, the recovery or reuse of the catalyst is facilitated. As the column, a tubular column or a groove-shaped column is preferably used.

It is preferred that in the above-mentioned method for manufacturing an organic material, in the second step, a reaction reagent or a solution of a reaction reagent for the organic reaction is introduced into a first end of the container or the column and discharged from a second end which is opposite end of the first end.

EMBODIMENTS

A synthesis of catalyst Cat-1 represented by the following formula (1) according to an embodiment of the present invention will be described. Catalyst Cat-1 does not contain a metal atom in its chemical structure, and has a structure in which an onium salt having a plurality of binaphthyl groups bonds to a polymer chain. One of the plurality of binaphthyl groups bonds to the polymer chain through at least one covalent bond or through a side chain containing an ether bond, which is a type of an organic group. Specifically, the catalyst has two axially chiral binaphthyl groups, and has an alkylene group such as a methylene group at 2-position carbon atom and at 2'-position carbon atom of each of the two binaphthyl groups. The alkylene group bonds to a nitrogen atom to form a spiro structure. Accordingly, the nitrogen atom has four bonds and is a cation center of the onium salt.

The side chain between the onium salt and the polymer chain bonds to a binaphthyl group which does not have a substituent such as an aryl group at 3-position carbon atom or 3'-position carbon atom. Specifically, the side chain bonds to the 6-position of the binaphthyl group which does not have a substituent such as an aryl group at 3- or 3'-position. The onium salt and the polymer chain of the catalyst according to some embodiments of the present invention are connected by an organic group, and the organic group has a plurality of carbon atoms. In Cat-1, the side chain is a linear alkyl group including a bond of 6 carbon atoms.

Each of the binaphthyl group located on the onium salt side of the alkyl group and the phenyl group located on the polymer chain side of the alkyl group bonds to the alkyl chain through an ether bond.

Figure 6:
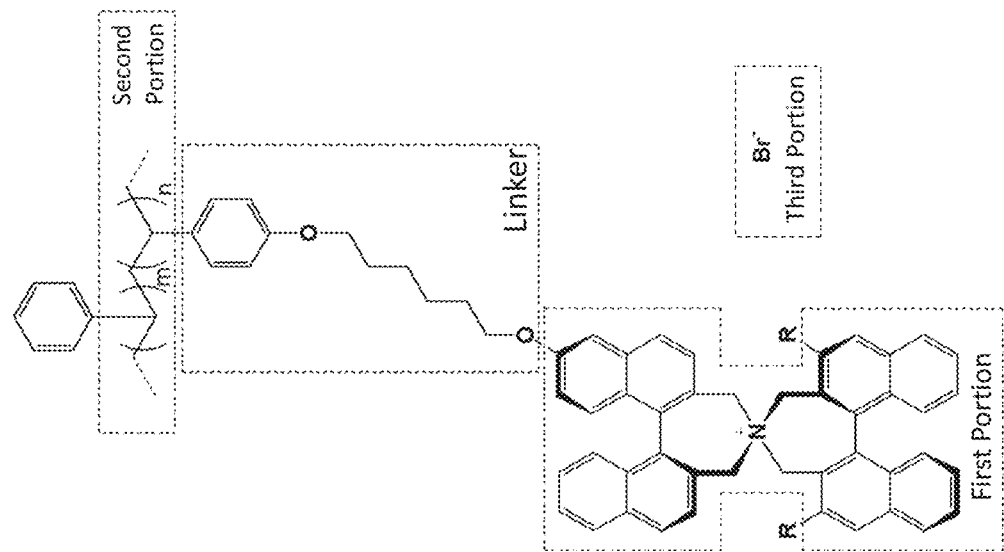
FIG. 6 illustrates a typical compound according to one embodiment of the present invention.
Figure 7:
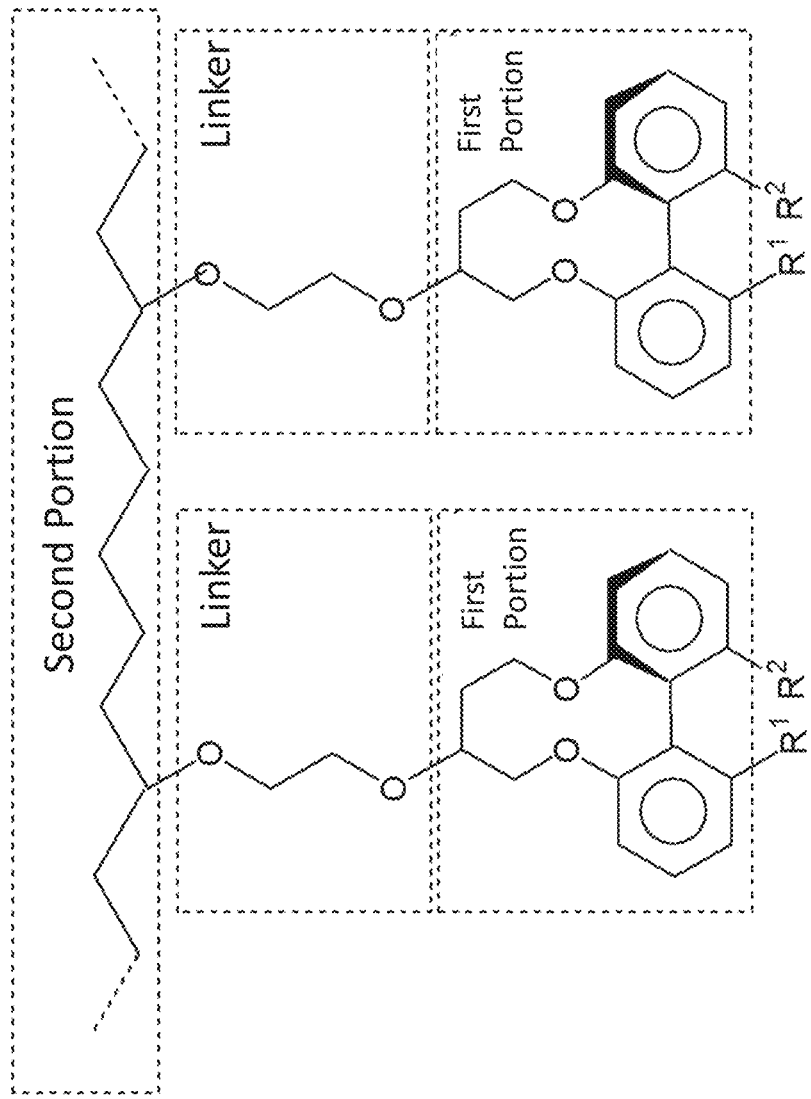
FIG. 7 illustrates a typical compound according to one embodiment of the present invention.
Figure 8:
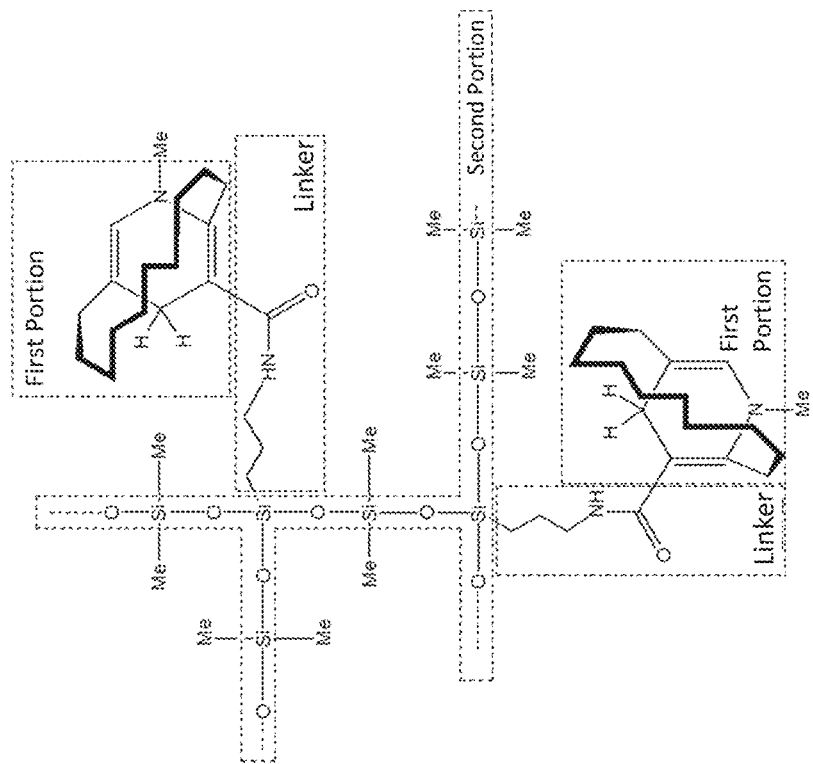
FIG. 8 illustrates a typical compound according to one embodiment of the present invention.
Figure 9:
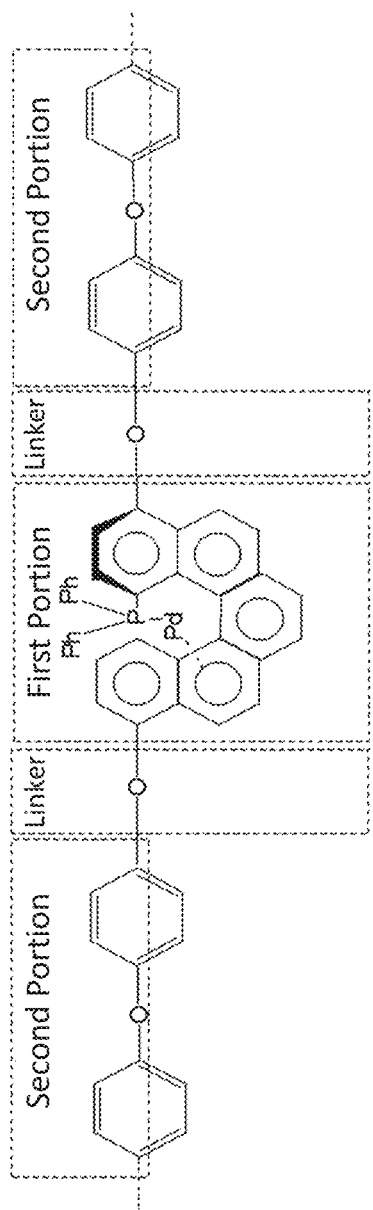
FIG. 9 illustrates a typical compound according to one embodiment of the present invention.
Figure 10:
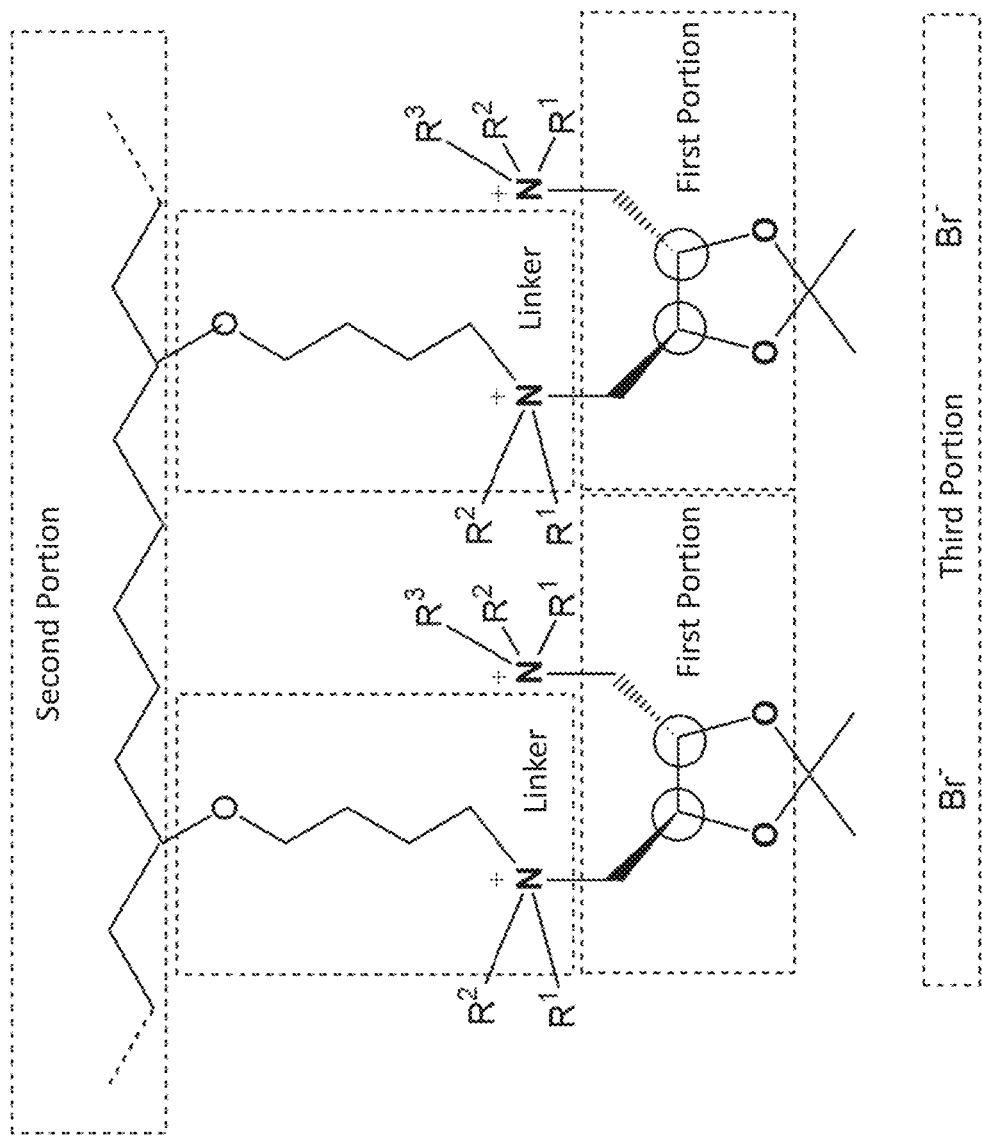
FIG. 10 illustrates a typical compound according to one embodiment of the present invention.

In the catalyst according to some embodiments of the present invention, as described in the explanation of the compounds exemplified in FIG. 6, a portion connecting a substituent inducing chirality with the polymer chain is referred to the linker. Specifically, in Cat-1, a portion including an oxygen atom bonding to a carbon atom at 6-position of the binaphthyl group, an alkyl group bonding to the oxygen atom and a phenyl group bonding to the alkyl group through an ether bond is defined as the linker.

A number of bonds from the nitrogen atom at the cation center to the polymer chain, in shortest, is 20 bonds. In this case, a number of atoms constituting the linker is 19, which is a number by counting atoms from a carbon atom bonding to the nitrogen atom to a carbon atom of a phenyl group skeleton bonding directly to the polymer chain. Among these 19 atoms constituting the linker, a portion from an oxygen atom bonding to the carbon atom at 6-position of the binaphthyl skeleton to an oxygen atom bonding to the phenyl ring bonding to the polymer chain is a hydrocarbon group including a bond of 6 carbon atoms. When this compound is used as a catalyst of an asymmetric reaction which must obtain selectivity within a slight energy difference, it is possible to reduce an influence from the polymer chain in the reaction proceeding in a vicinity of the cation center by increasing the distance between the polymer chain and the highly polar cation center, an optical yield of an obtained product may be improved. Therefore, it is preferred that the number of constituent atoms of the linker is 4 or more, and the number of carbon atoms of the hydrocarbon group contained in the linker is 3 or more. It is further preferred that the number of the carbon atoms of the hydrocarbon group contained in the linker is 6 or more.

[Chem. 1]

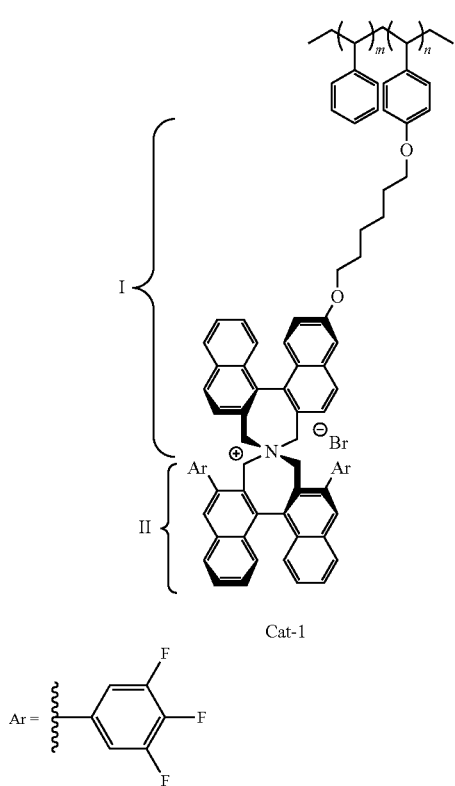

For example, Cat-1 can be synthesized by synthesizing a segment I and a segment II separately, bonding the segment I and the segment II to form an ammonium salt having two binaphthyl groups, and then bonding the ammonium salt, as at least one part of a side chain, to the polymer chain.

The segment I can be synthesized by a synthetic process as illustrated in the following formula (2). Specifically, a hexane solution of 1.5 equivalents of n-butyllithium is added dropwise at −78° C. to Compound 1 having a methoxymethyl group (MOM group) as a protecting group at 2-position and 2'-position of a binaphthyl group and having a bromine atom as a halogen atom at 6-position of the binaphthyl group, in dehydrated tetrahydrofuran, and the mixture is stirred at room temperature for 4 hours. Thereafter, 2 equivalents of isopropoxyboronic acid pinacol ester is added dropwise at −78° C., and the mixture is stirred at room temperature for 12 hours to obtain Compound 2 having a boron atom at 6-position of the binaphthyl group, the boron atom bonding two oxygen atoms, in 85% yield based on Compound 1.

To this Compound 2, 12 equivalents of hydrogen peroxide and 3 equivalents of cesium carbonate are set to react in a mixed solvent of dichloromethane and ethanol at 35° C. for 2 hours to obtain Compound 3 having a hydroxy group at 6-position of the binaphthyl group in 88% yield based on Compound 2.

Compound 3 is dissolved in acetone, 10 equivalents of potassium carbonate and 5 equivalents of methyl iodide are added to this acetone solution of Compound 3, and the mixture is stirred at 50° C. for 18 hours to obtain Compound 4 having a methoxy group, which is an alkoxy group, at 6-position of the binaphthyl group is obtained in 90% yield based on Compound 3.

Compound 4 is dissolved in 1,4-dioxane to prepare a 1,4-dioxane solution of Compound 4. Concentrated hydrochloric acid is added dropwise to the 1,4-dioxane solution at room temperature and stirred at 50° C. for 6 hours to obtain Compound 5 in which the methoxymethyl groups as the protecting group of 2- and 2'-positions are deprotected, and 2- and 2'-positions are converted to hydroxy groups in 99% based on Compound 4.

Compound 5 is dissolved in methylene chloride to prepare a methylene chloride solution of Compound 5. To this methylene chloride solution, 3 equivalents of triethylamine is added, 2.5 equivalents of trifluoromethanesulfonic anhydride is added dropwise at 0° C., and then the mixture is stirred at room temperature for 1 hour to obtain Compound 6 in which 2- and 2'-positions of the binaphthyl group are converted to trifluoromethylsulfonyl groups in 99% yield based on Compound 5.

Compound 6 is dissolved in diethyl ether to prepare a diethyl ether solution of Compound 6. To the solution of Compound 6 in diethyl ether, 5 mol % of dichloro(1,3-bis (diphenylphosphino) propane)nickel (II) based on Compound 6 is added, and 6 equivalents of methylmagnesium iodide is added dropwise to the resulting ether solution at 0° C. The mixture is stirred at room temperature for 60 hours to obtain Compound 7 having a methyl group, which is an alkyl group, at each of 2- and 2'-position of the binaphthyl group in 75% yield based on Compound 6.

Compound 7 is dissolved in methylene chloride to prepare a methylene chloride solution of Compound 7. Boron tribromide is added dropwise to this methylene chloride solution of Compound 7 at 0° C., and stirred at room temperature for 12 hours to obtain Compound 8 in which the methoxy group at 6-position is converted to a deprotected hydroxy group in 95% yield based on Compound 7.

Compound 8 is dissolved in acetone to prepare an acetone solution of Compound 8. An equivalent amount of potassium carbonate and 5 equivalents of 6-bromo-1-hexanol are added to the acetone solution of Compound 8, and the mixture is stirred at 70° C. for 18 hours to obtain Compound 9 having 6-hydroxyhexyl group, which is an alkoxy group having a hydroxy group at an end, at 6-position of the binaphthyl group in 85% yield based on Compound 8.

Compound 9 is dissolved in benzene to prepare a benzene solution of Compound 9. 10 mol % of 2,2-azobis (isobutyronitrile) and 2 equivalents of N-bromosuccinimide are added to the benzene solution of Compound 9. The mixture is heated to refluxed for 4 hours to obtain Compound 10 having a bromomethyl group at 2- and 2'-positions in 90% yield based on Compound 9.

[Chem. 2]

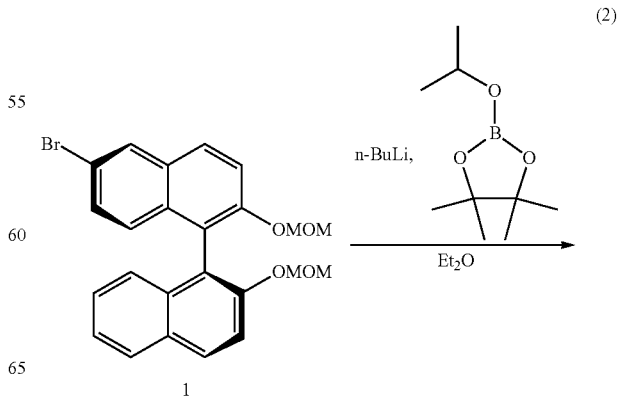

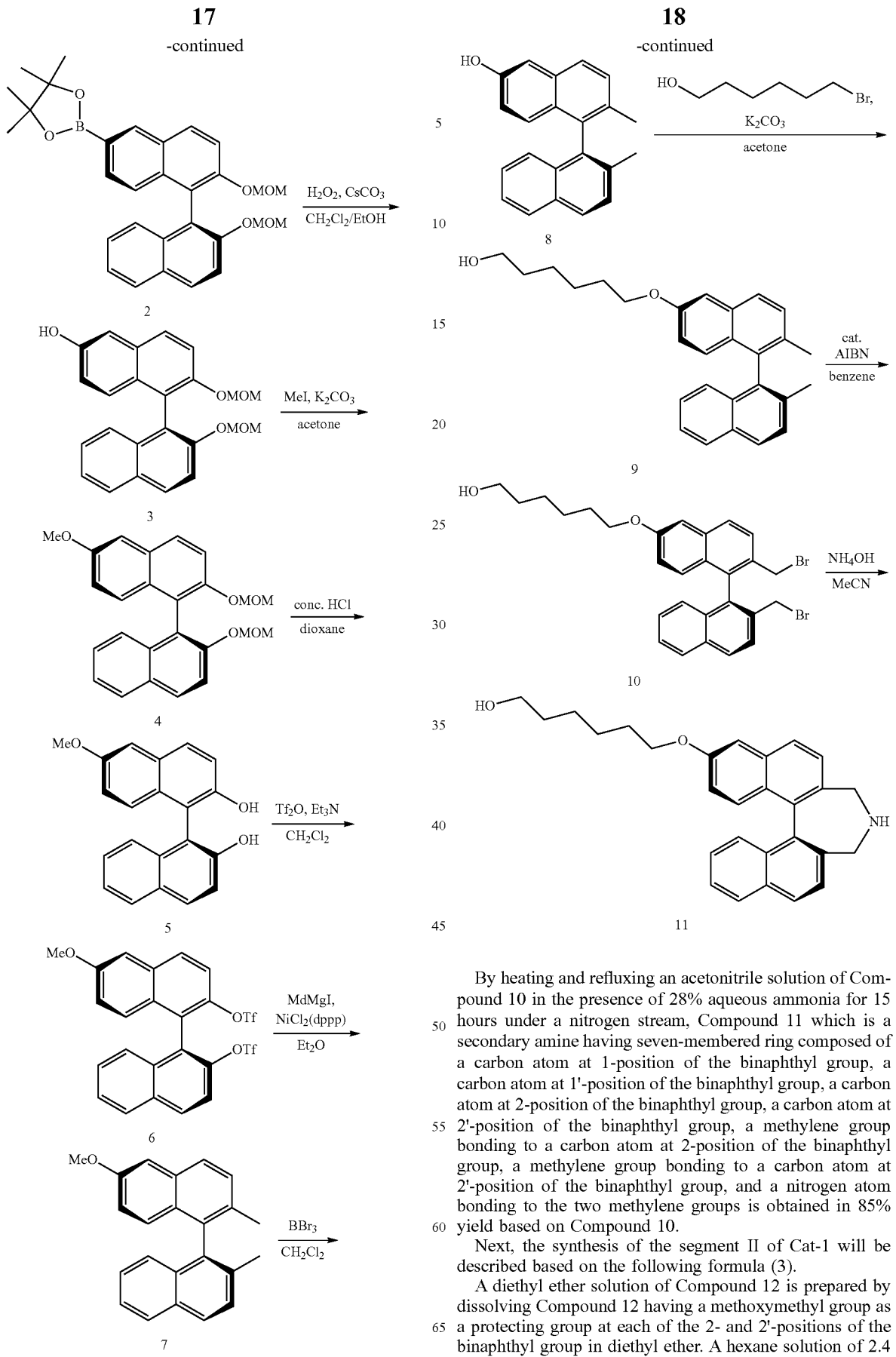

By heating and refluxing an acetonitrile solution of Compound 10 in the presence of 28% aqueous ammonia for 15 hours under a nitrogen stream, Compound 11 which is a secondary amine having seven-membered ring composed of a carbon atom at 1-position of the binaphthyl group, a carbon atom at 1'-position of the binaphthyl group, a carbon atom at 2-position of the binaphthyl group, a carbon atom at 2'-position of the binaphthyl group, a methylene group bonding to a carbon atom at 2-position of the binaphthyl group, a methylene group bonding to a carbon atom at 2'-position of the binaphthyl group, and a nitrogen atom bonding to the two methylene groups is obtained in 85% yield based on Compound 10.

Next, the synthesis of the segment II of Cat-1 will be described based on the following formula (3).

A diethyl ether solution of Compound 12 is prepared by dissolving Compound 12 having a methoxymethyl group as a protecting group at each of the 2- and 2'-positions of the binaphthyl group in diethyl ether. A hexane solution of 2.4 equivalents of n-butyllithium is added dropwise to the diethyl ether solution of Compound 12 at room temperature and the mixture is stirred at room temperature for 4 hours. Thereafter, 3 equivalents of trimethoxyborane is added dropwise at −78° C. and the mixture is stirred at room temperature for 12 hours.

Subsequently, the solvent is replaced with benzene, then 12 equivalents of hydrogen peroxide is dropped thereto, and the mixture is stirred at 80° C. for 2 hours to obtain Compound 13 in 56% yield based on Compound 12.

Compound 13 is dissolved in acetone, 10 equivalents of potassium carbonate and 10 equivalents of methyl iodide are added to the acetone solution of Compound 13, and the mixture is stirred at 50° C. for 18 hours to obtain Compound 14 having a methoxy group, which is an alkoxy group, at 3- and 3'-positions of the binaphthyl group in 90% yield based on Compound 13.

Compound 14 is dissolved in 1,4-dioxane to prepare a 1,4-dioxane solution of Compound 14. Concentrated hydrochloric acid is added dropwise to the 1,4-dioxane solution at room temperature, and the mixture is stirred at 50° C. for 6 hours to obtain Compound 15 in which the methoxy groups as the protecting group of 2- and 2'-positions are deprotected and 2- and 2'-positions of the binaphthyl group are converted to hydroxy groups is obtained in 99% yield based on Compound 14.

Compound 15 is dissolved in methylene chloride to prepare a methylene chloride solution of Compound 15. To this methylene chloride solution, 6 equivalents of triethylamine, and 5.5 equivalents of trifluoromethanesulfonic anhydride is added dropwise at 0° C., and then the mixture is stirred at room temperature for 1 hour to obtain Compound 16 in which 2- and 2'-positions of the binaphthyl group are converted to trifluoromethylsulfonyl groups in 99% yield based on Compound 15.

Compound 16 is dissolved in dehydrated diethyl ether to prepare a diethyl ether solution of Compound 16. To the diethyl ether solution of Compound 16, 5 mol % of dichloro(1,3-bis(diphenylphosphino)propane) nickel (II) based on Compound 16 is added, and 6 equivalents of methylmagnesium iodide is added dropwise to the resulting ether solution at 0° C., and then the mixture is stirred at room temperature for 60 hours to obtain Compound 17 having a methyl group, which is an alkyl group, at 2- and 2'-positions of the binaphthyl group in 75% yield based on Compound 16.

Compound 17 is dissolved in methylene chloride to prepare a methylene chloride solution of Compound 17. Boron tribromide is added dropwise to the methylene chloride solution of Compound 18 at 0° C. and stirred at room temperature for 12 hours to obtain Compound 18 in which alkoxy groups at 3- and 3'-positions of the binaphthyl group are deprotected and converted to hydroxy groups in 95% yields based on Compound 17.

Compound 18 is dissolved in methylene chloride to prepare a methylene chloride solution of Compound 18. To the methylene chloride solution, 3 equivalents of triethylamine is added, 2.5 equivalents of trifluoromethanesulfonic anhydride is added dropwise at 0° C., and then the mixture is stirred at room temperature for 1 hour to obtain Compound 19 in which 3- and 3'-positions of the binaphthyl group are converted to trifluoromethylsulfonyl groups in 99% yield based on Compound 18.

Compound 19 is dissolved in tetrahydrofuran to prepare a tetrahydrofuran solution of Compound 19. To the tetrahydrofuran solution of Compound 19, 5 mol % of tetrakis(triphenylphosphine)palladium (0) based on Compound 19, 3.5 equivalent of 1-bromo-3,4,5-trifluorobenzene and 4 equivalents of potassium phosphate hydrate are added, and stirred at 65° C. for 24 hours to obtain Compound 20 having 3,4,5-trifluorophenyl groups, which are aryl groups, at each of the 3- and 3'-positions of the binaphthyl group.

Compound 20 is dissolved in benzene to prepare a benzene solution of Compound 20. 10 mol % of 2,2-azobis(isobutyronitrile) and 2.3 equivalents of N-bromosuccinimide are added to the benzene solution of Compound 20. By heating and refluxing this mixture for 4 hours, Compound 21 having bromomethyl groups at 2- and 2'-positions is obtained in 90% yield based on Compound 20.

[Chem. 3]

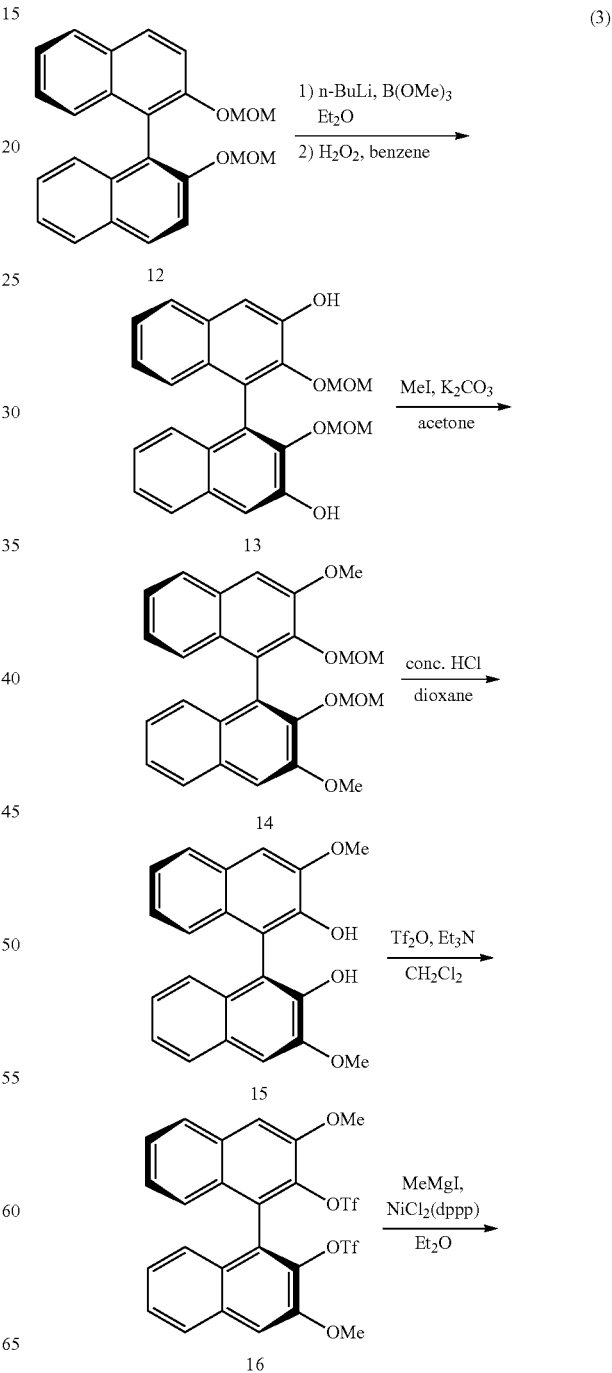

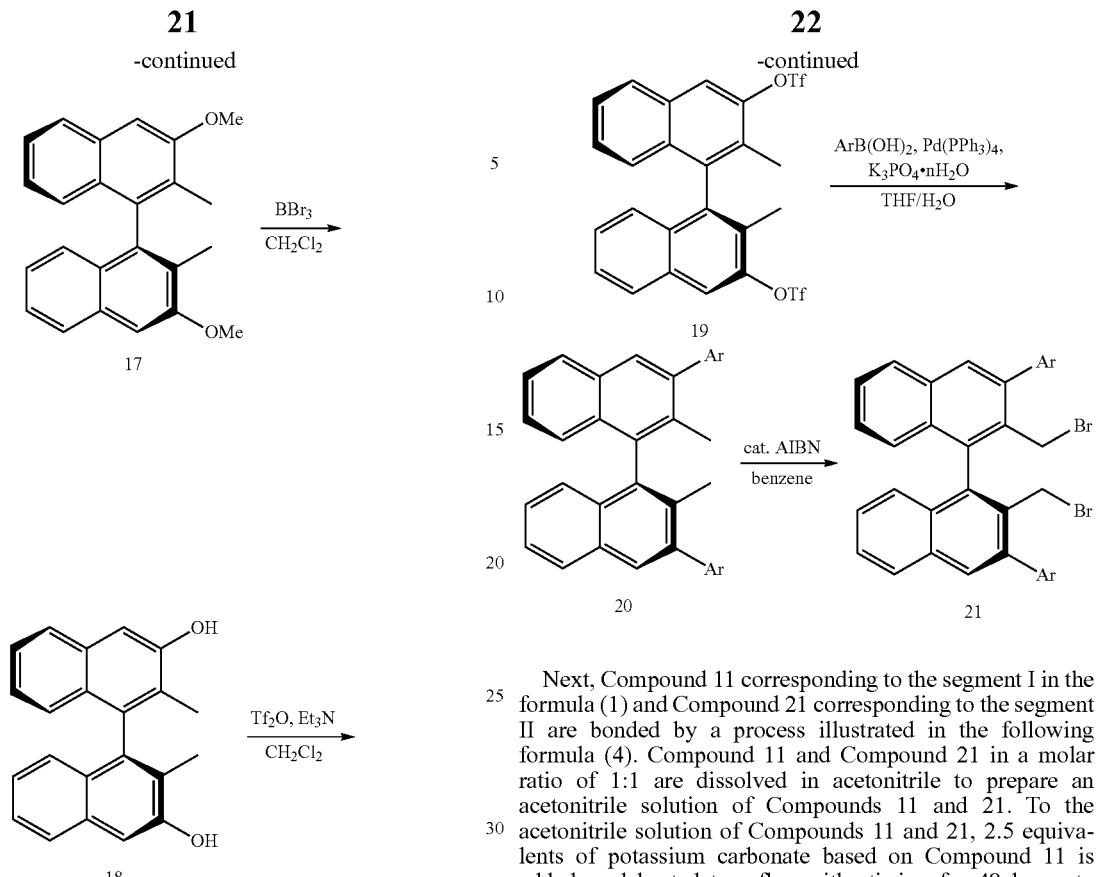

Next, Compound 11 corresponding to the segment I in the formula (1) and Compound 21 corresponding to the segment II are bonded by a process illustrated in the following formula (4). Compound 11 and Compound 21 in a molar ratio of 1:1 are dissolved in acetonitrile to prepare an acetonitrile solution of Compounds 11 and 21. To the acetonitrile solution of Compounds 11 and 21, 2.5 equivalents of potassium carbonate based on Compound 11 is added, and heated to reflux with stirring for 48 hours to obtain Compound 22 which is a spiro quaternary ammonium compound having two binaphthyl groups in 90% yield based on Compound 11.

(4)

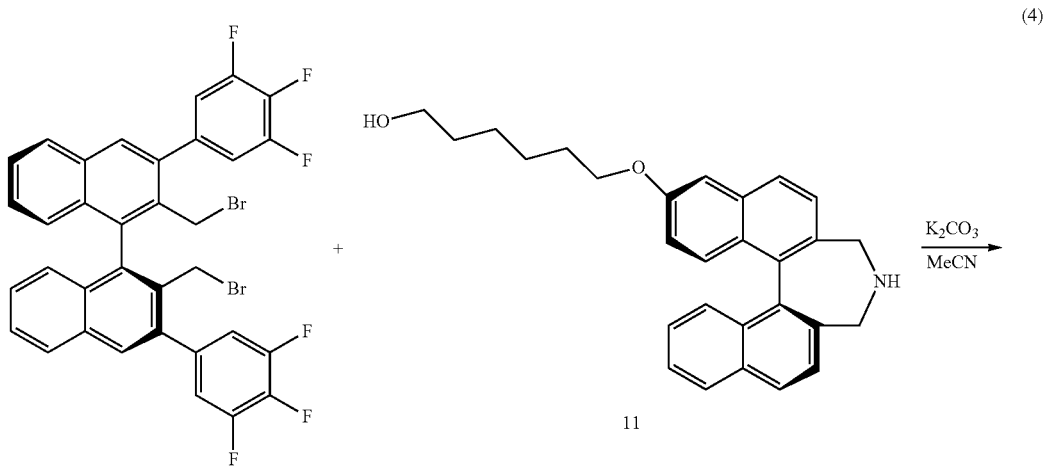

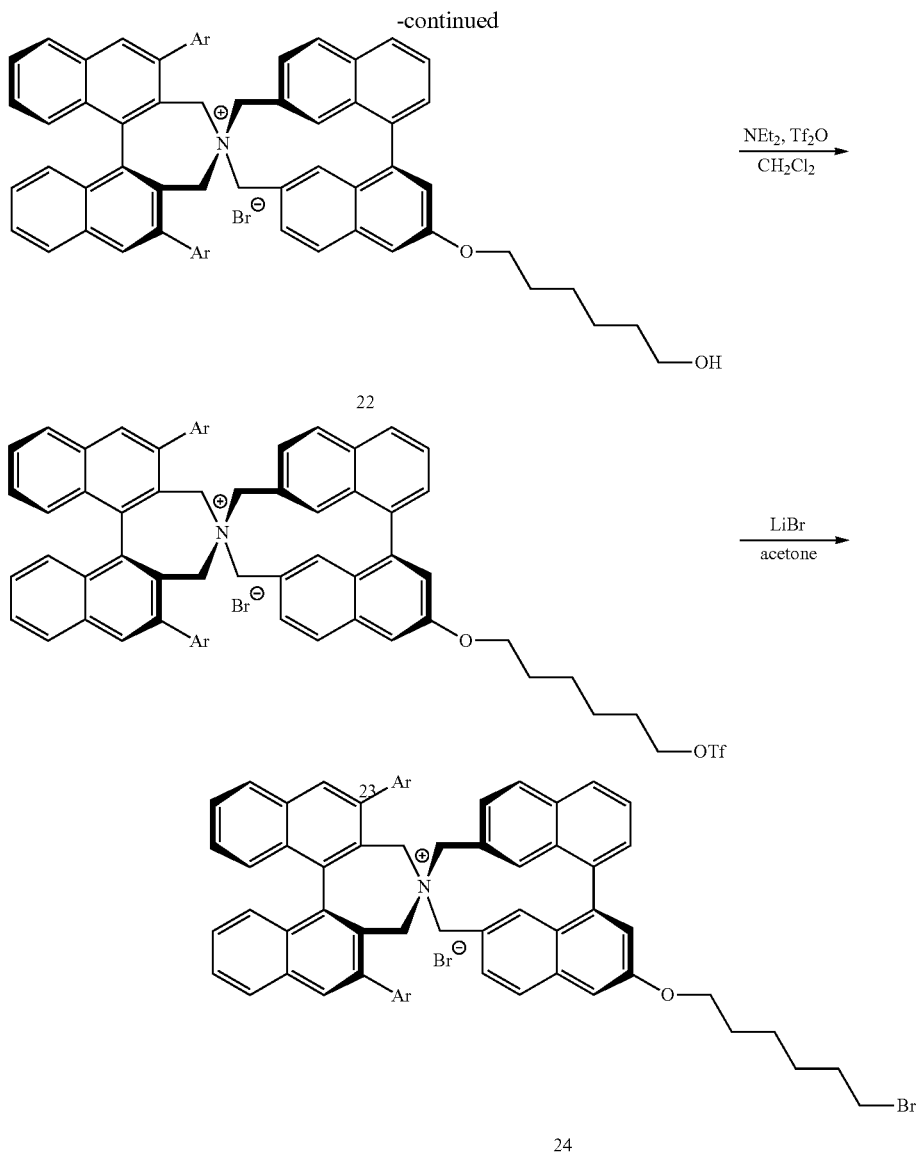

Compound 22 is dissolved in methylene chloride to prepare a methylene chloride solution of Compound 22. To this methylene chloride solution of Compound 22, 3 equivalents of triethylamine based on Compound 22 is added, 2.5 equivalents of trifluoromethanesulfonic anhydride based on Compound 22 is added dropwise to the mixture at 0° C., and then the mixture is stirred for 1 hour to obtain Compound 23 having an alkyl group at 6-position of a binaphthyl group not having an aryl group at 3- and 3'-positions among the two binaphthyl groups, the alkyl group having a trifluoromethylsulfonyl group at the end, in 95% yield based on Compound 22.

Compound 23 is dissolved in acetone to prepare an acetone solution of Compound 23. To the acetone solution of Compound 23, 20 equivalents of lithium bromide based on Compound 23 is added and heated to reflux for 24 hours with stirring to obtain Compound 24 having an alkyl group at 6-position of the binaphthyl group not having an aryl group at 3- and 3'-positions among the two binaphthyl groups, the alkyl group having a bromine atom, which is a halogen atom, bonds at the end, in 90% yield based on Compound 23.

Compound 24 is connected with the polymer chain by a process illustrated in the following formula (5). Compound 24 is dissolved in acetonitrile to prepare a dimethyl sulfoxide solution of Compound 24. 2.5 equivalents of potassium carbonate and 1.2 equivalents of p-hydroxystyrene based on Compound 24 are added to the dimethyl sulfoxide solution of Compound 24, and the mixture is heated to reflux with stirring for 48 hours to obtain Compound 25 which is a spiro-type quaternary ammonium compound having two binaphthyl groups and an alkoxy group at 6-position of the binaphthyl group not having an aryl group at 3- and 3'-positions among the two binaphthyl groups, the alkoxy group having a 4-vinylphenoxy group at the end, in 90% yield based on Compound 24.

Compound 25 is dissolved in anisole to prepare an anisole solution of Compound 25. 10 mol % of 2,2-azobis (isobutyronitrile) based on Compound 26 and 4 equivalents of styrene based on Compound 25 are added to the anisole solution of Compound 25, and the mixture is heated to reflux under a nitrogen stream for 16 hours to obtain Cat-1, which is a copolymer.

Further, styrene may have a substituent on at least one of two carbon atoms of an olefin moiety, and may have at least one substituent on benzene.

Further, a monomer having an aryl group other than benzene such as a vinyl naphthalene derivative and a vinyl anthracene which may have a substituent on the olefin or on the aryl group may be used instead of or in addition to styrene.

[Chem. 5]

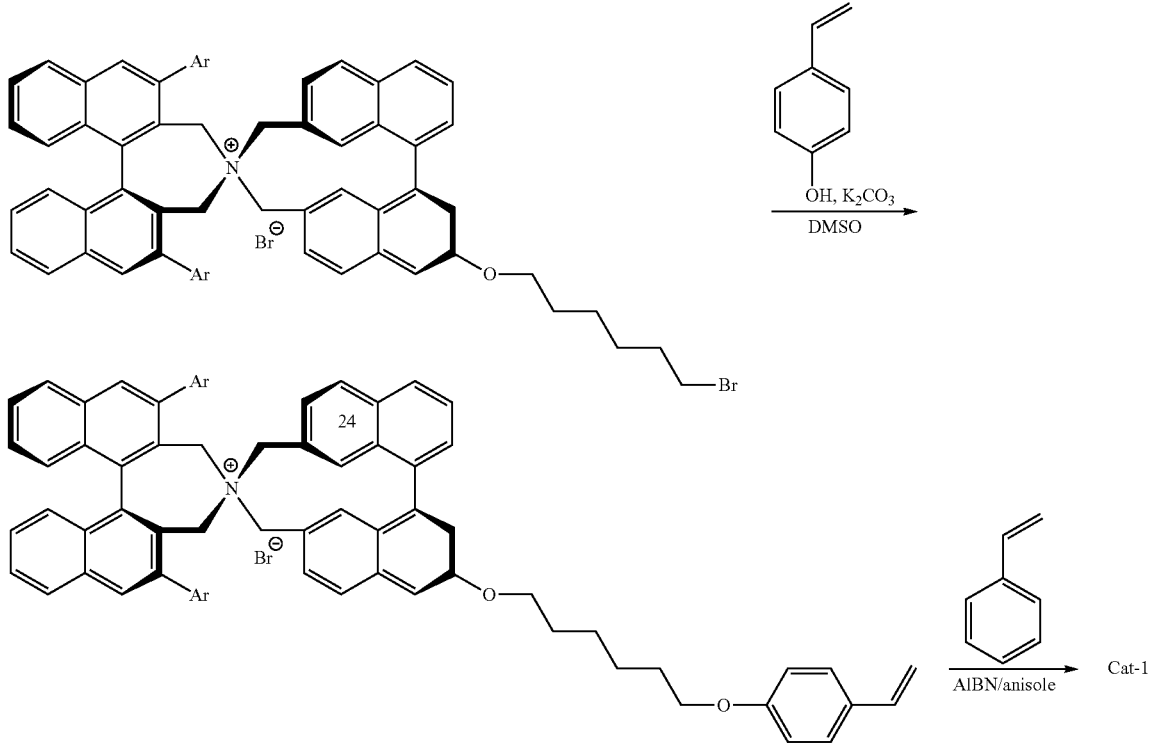

(5)

For example, a monomer having a plurality of polymerizable groups such as divinylbenzene may be added instead of styrene or in addition to styrene during the reaction of polymerizing Compound 25. According to this, for example, a catalyst having improved insolubility to a solvent such as Cat-2 illustrated in the following formula (6) with improved degree of crosslinking of Cat-1 is obtained.

In Cat-2, a polymer chain having the spiro-type quaternary ammonium, which is a catalyst center, on a side chain bonds through a crosslinking group whose constituent material is mainly composed of a plurality of carbon atoms.

[Chem. 6]

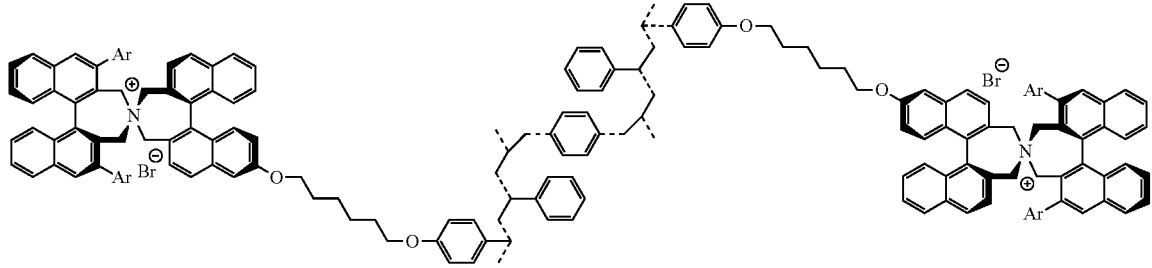

(6)

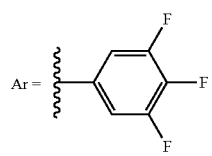

Next, synthesis of Cat-3 having only one binaphthyl group, having an alkyl group at the nitrogen atom which is a cation center of ammonium, and bonding to a polymer chain through an organic group such as the alkyl group and an ether bond will be explained according to a following formula (7). In Cat-3, a portion containing: the alkyl group bonding to the nitrogen atom as the cation center; and a phenyl group bonding to the alkyl group through the ether bond and bonding to the polymer chain is defined as the linker connecting the cation center of the onium salt with the polymer chain.

A number of bonds from the nitrogen atom of the cation center to the polymer chain, in shortest, is 12 bonds. In this case, a number of atoms constituting the linker is 11, which is a number by counting atoms from a carbon atom bonding to the nitrogen atom to a carbon atom of a phenyl group skeleton bonding directly to the polymer chain. Among these 11 atoms constituting the linker, a portion from an oxygen atom bonding to a carbon at 6-position of binaphthyl group skeleton to an oxygen atom bonding to the benzene ring bonding to the polymer chain is a hydrocarbon group constituted by bonding of 6 carbon atoms.

When this compound is used as a catalyst of an asymmetric reaction which must obtain selectivity within a slight energy difference, it is possible to reduce an influence from the polymer chain in the reaction proceeding in a vicinity of the cation center by increasing the distance between the polymer chain and the highly polar cation center, and an optical yield of an obtained product may be improved. Therefore, it is preferred that the number of constituent atoms of the linker is 4 or more, and the number of carbon atoms of the hydrocarbon group contained in the linker is 3 or more. It is further preferred that the number of the carbon atoms of the hydrocarbon group contained in the linker is 6 or more.

Compound 21 having bromomethyl groups at 2- and 2'-positions of the binaphthyl groups and 1.5 equivalents of 6-amino-1-hexanol, which is a primary amine having a hydroxyl group at an end, and 3 equivalents of potassium carbonate based on Compound 21 are added and stirred at 50° C. for 5 hours to obtain Compound 26 in which an alkyl group having a hydroxy group at the end bonds to the nitrogen atom in 62% yield based on Compound 21.

To Compound 26, 1.3 equivalents of triphenylphosphine and 1.3 equivalents of carbon tetrabromide based on Compound 27 are added, and stirred at room temperature for 3 hours to obtain Compound 27 in 70% yield based on Compound 26.

Compound 27 is dissolved in acetonitrile to prepare an acetonitrile solution of compound 27. Hexyl bromide, which is an alkyl halide, is added to the acetonitrile solution and the mixture is heated to reflux with stirring for 24 hours to obtain Compound 28 which is an ammonium salt having the binaphthyl group, an alkyl group and an alkyl group having a halogen atom at an end is obtained in 85% yield based on Compound 27.

Compound 28 is dissolved in dimethylsulfoxide to prepare a dimethylsulfoxide solution of Compound 28. 2.5 equivalents of potassium carbonate and 1.2 equivalents of p-hydroxystyrene based on Compound 28 are added to the dimethyl sulfoxide solution of Compound 28, and the mixture is heated to reflux with stirring for 48 hours to obtain Compound 29 which is a quaternary ammonium compound having an alkoxy group on the nitrogen atom, the alkoxy group having a 4-vinylphenoxy group at the end in 90% yield based on Compound 28.

Compound 29 is dissolved in anisole to prepare a toluene solution of compound 29. 10 mol % of 2,2-azobis (isobutyronitrile) based on Compound 29 and 4 equivalents of styrene based on Compound 29 are added to the anisole solution of Compound 29, and the mixture is heated to reflux under a nitrogen stream for 16 hours to obtain Cat-3, which is a copolymer.

[Chem. 7]

(7)

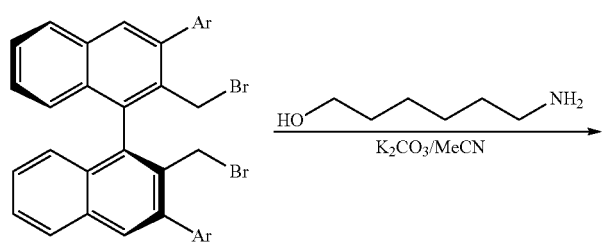

-continued
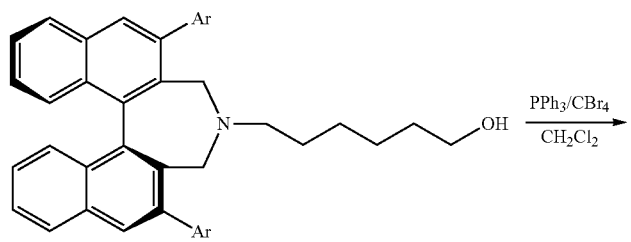
26
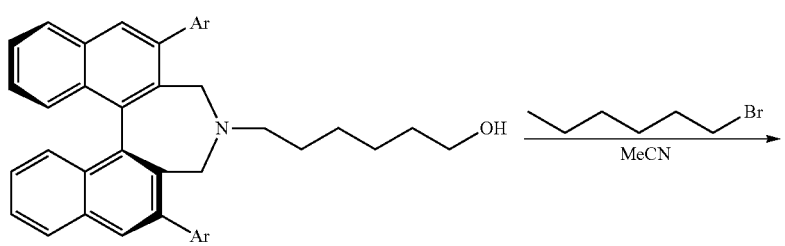
27
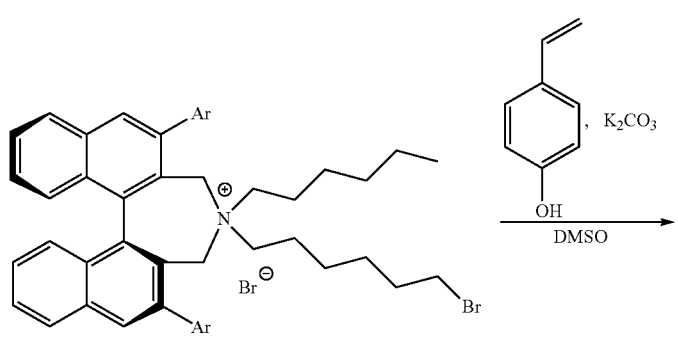
28
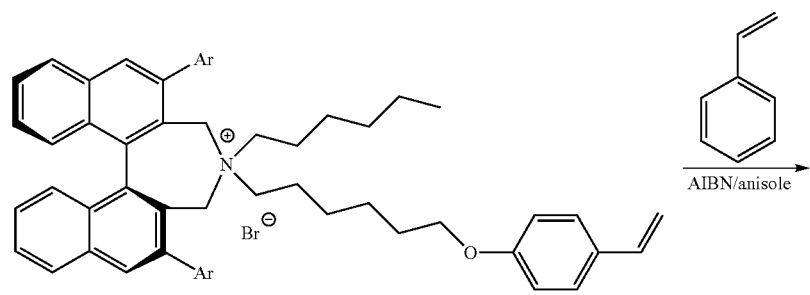
29

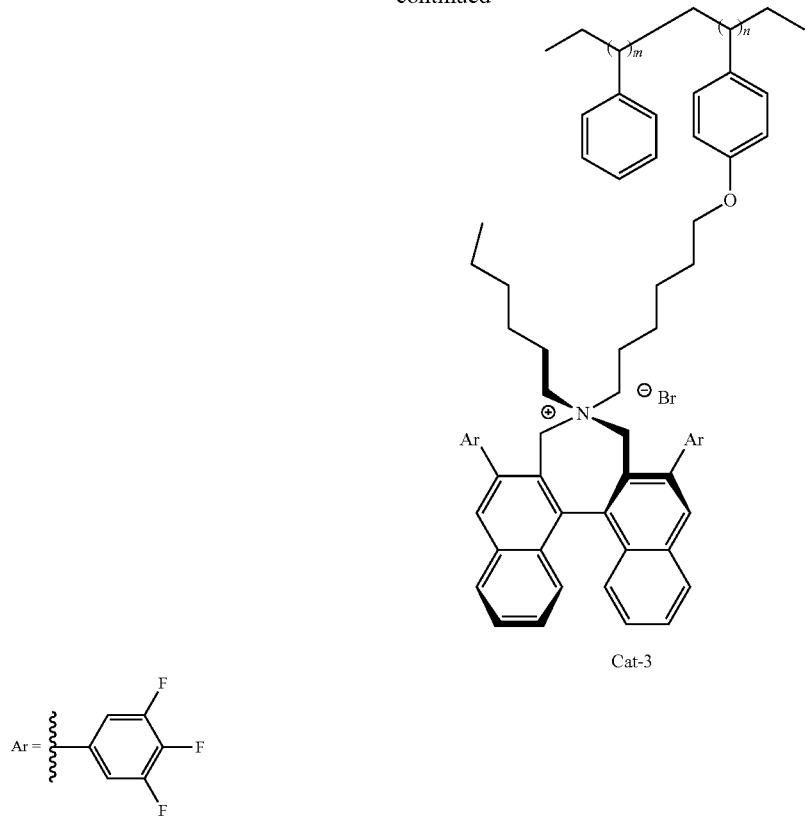

Cat-3

Ar = [3,4,5-trifluorophenyl]

For example, during the polymerization reaction of Compound 29, a monomer having a plurality of polymerizable groups such as divinylbenzene may be added as a crosslinking agent instead of styrene or in addition to styrene. According to this, for example, a catalyst having improved insolubility to a solvent such as Cat-4 illustrated in the following formula (8) with improved degree of crosslinking of Cat-3 is obtained.

In Cat-4, the ammonium salt having a seven-membered ring composed of a carbon atom at 1-position contained in the binaphthyl group skeleton which is a catalytic center, a carbon atom at 1'-position of the binaphthyl group, a carbon atom at 2-position of the binaphthyl group, a carbon atom at 2'-position of the binaphthyl group, methylene groups bonding to each of the carbon atom at 2- and 2'-positions of the binaphthyl group, respectively, and a nitrogen atom bonds to a polymer chain through a crosslinking group whose constituent material is mainly composed of a plurality of carbon atoms.

[Chem. 8]

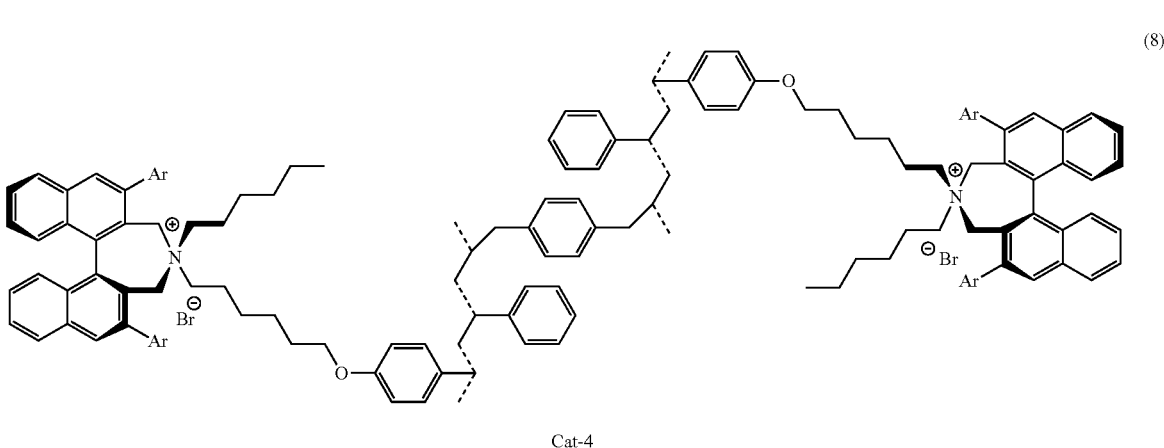

(8)

Cat-4

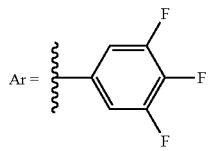

Cat-3 can also be synthesized by the following formula (9). 1.5 equivalents of hexylamine, which is a primary alkylamine, and 3 equivalents of potassium carbonate based on Compound 21 are added to an acetonitrile solution of Compound 21 having bromomethyl groups at each of the 2- and 2'-positions of the binaphthyl group, and the mixture is stirred at 50° C. for 5 hours to obtain Compound 30, which is a cyclic amine compound in which an alkyl group bonds to a nitrogen atom and methylene groups at 2- and 2'-positions of the binaphthyl group bond to the nitrogen atom in 70% yield based on Compound 21.

1.5 equivalents of 6-bromo-1-hexanol is added to an acetonitrile solution of Compound 30, and the mixture is heated to reflux with stirring for 48 hours to obtain Compound 31, which is an ammonium salt having a binaphthyl group and an alkyl group on the nitrogen atom of the cation center, the alkyl group having a hydroxy group at an end, in 45% yield.

To a methylene chloride solution of Compound 31, 3 equivalents of triethylamine is added, then 2.5 equivalents of trifluoromethanesulfonic anhydride is added dropwise at 0° C., and the mixture is stirred at room temperature for 1 hour to quantitatively obtain Compound 32 in which an alkyl group having a trifluoromethanesulfonyl group at the end bonds to the nitrogen atom of the cation center of the ammonium salt.

20 equivalents of lithium bromide is added to an acetone solution of Compound 32, and the mixture is heated to reflux with stirring for 24 hours to obtain Compound 28 in 95% yield.

Compound 28 is dissolved in dimethylsulfoxide to prepare a dimethylsulfoxide solution of compound 28. 2.5 equivalents of potassium carbonate and 1.2 equivalents of p-hydroxystyrene based on Compound 28 are added to the dimethyl sulfoxide solution of Compound 28, and the mixture is heated to reflux with stirring for 48 hours to obtain Compound 29 which is a quaternary ammonium compound having an alkoxy group on the nitrogen atom, the alkoxy group having a 4-vinylphenoxy group at the end in 90% yield based on Compound 28.

Compound 29 is dissolved in anisole to prepare an anisole solution of Compound 29. 10 mol % of 2,2-azobis (isobutyronitrile) based on Compound 29 and 4 equivalents of styrene based on Compound 29 are added to the anisole solution of Compound 29, and the mixture is heated to reflux under a nitrogen stream for 16 hours to obtain Cat-3, which is a copolymer.

For example, during the polymerization reaction of Compound 29, a monomer having a plurality of polymerizable groups such as divinylbenzene may be added as a crosslinking agent instead of styrene or in addition to styrene. According to this, Cat-4 having improved insolubility to a solvent can be obtained.

[Chem. 9]

(9)

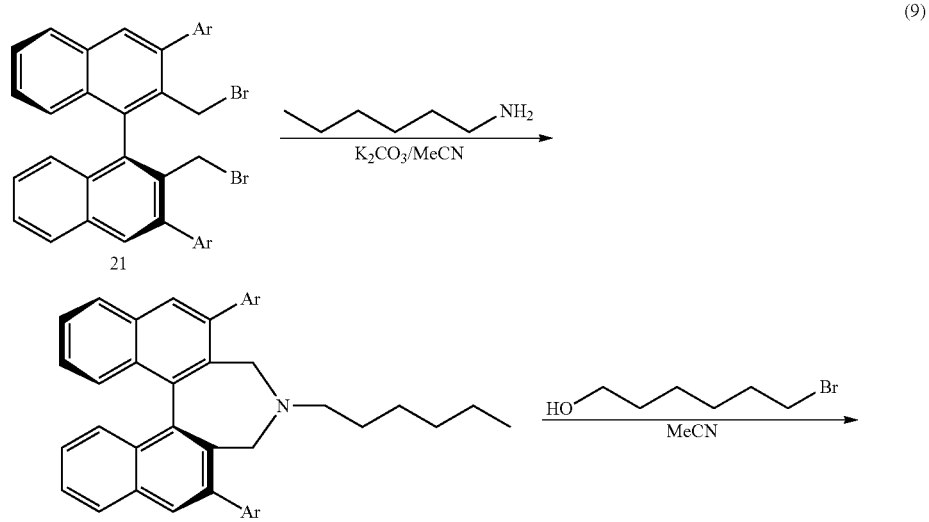

-continued

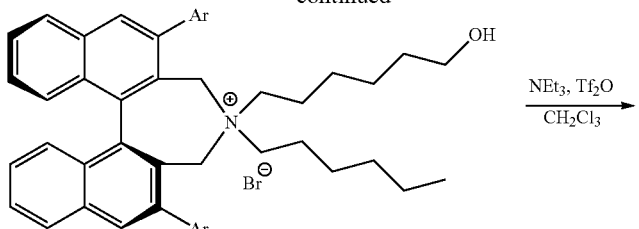

31

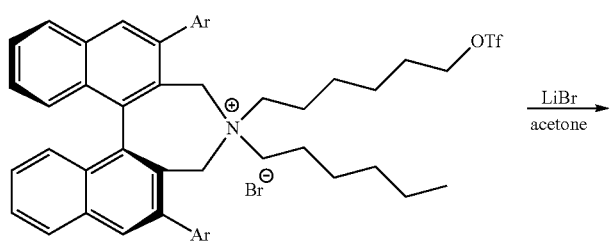

32

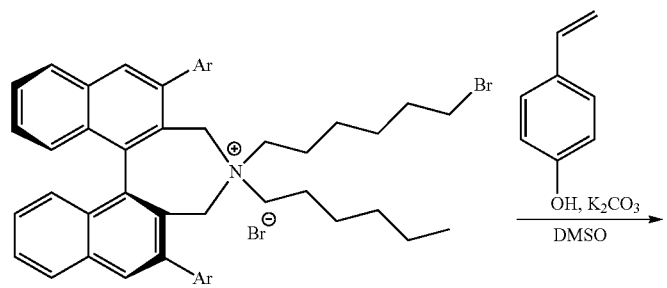

28

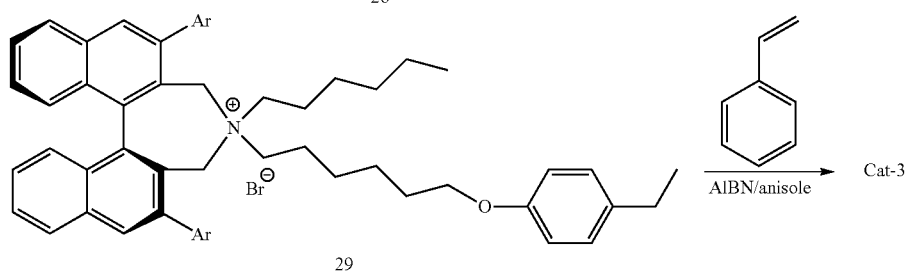

29

Compound 31 can also be synthesized by a route illustrated in the following formula (10).

A solution of Compound 21 in N,N-dimethylformamide is prepared, 0.95 equivalents of 2-nitrobenzenesulfonamide and 4 equivalents of potassium carbonate based on Compound 22 are added to the N,N-dimethylformamide solution of Compound 21, and then the mixture is stirred at 60° C. for 24 hours to obtain Compound 33 in which a 2-nitrobenzenesulfonyl group, which is one of protecting groups for an amino group, bonds to the nitrogen atom in 85% yield.

1.1 equivalents of benzenethiol and 2 equivalents of calcium carbonate are added to the obtained compound 33, and the mixture is stirred at 40° C. for 1 hour to obtain Compound 34 which is a secondary amine having a seven-membered ring composed of a carbon atom at 1-position of the binaphthyl group, a carbon atom at 1'-position of the binaphthyl group, a carbon atom at 2-position of the binaphthyl group, a carbon atom at 2'-position of the binaphthyl group, a methylene group bonding to a carbon atom at 2-position of the binaphthyl group, a methylene group bonding to a carbon atom at 2'-position of the binaphthyl group and a nitrogen atom bonding to the two methylene groups in 79% yield based on Compound 33.

4 equivalents of potassium carbonate, 0.95 equivalents of 1-bromohexane, which is a hydrocarbon compound having halogen atoms, based on Compound 34 are added to an acetonitrile solution of Compound 34, and the mixture is stirred at 45° C. for 5 hours, then 1.2 equivalents of 6-bromo-1-hexanol, which has a plurality of functional groups such as a hydroxy group and a halogeno group at the both ends is added and heated to reflux with stirring for 48 hours to obtain Compound 31 in 58% yield based on Compound 34.

Compound 31 can be further converted to Compound 32 and then Compound 28 as illustrated in the formula (9).

[Chem. 10]

(10)

Compound 31 can also be synthesized by a process illustrated in the following formula (11). 2 equivalents of 6-hexylamino-1-hexanol, which is a secondary amine having an alkyl group having a functional group such as a hydroxy group, based on Compound 21, and 2.5 equivalents of potassium carbonate based on Compound 22 are added to an acetonitrile solution of compound 21, and heated to reflux for 48 hours to obtain Compound 31 in 87% yield.

[Chem. 11]

(11)

As a method for insolubilizing of the polymer including the catalytic center described above, there is a method illustrated in the following formula (12). Cat-5 is obtained by this method. The synthesis is as follows.

0.624 g of an oil in which sodium hydride dispersed (content of sodium hydride=40%), 0.625 g of polyhydroxystyrene (weight-average molecular weight=25000) and a catalytic amount of N, N-dimethylformamide are stirred in tetrahydrofuran at room temperature for 15 minutes. Then, a tetrahydrofuran solution of Compound 28 (44 mg; 0.05 mmol) is added at room temperature and stirred at 40° C. for 2 hours. Thereafter, 0.263 g of 1,4-bis(bromomethyl)benzene (0.263 g; 1.0 mmol) having a plurality of alkyl groups containing a halogen atom as a crosslinking agent is added dropwise at 40° C. and stirred at 40° C. for 18 hours. Then, 1 mL of methyl iodide is added dropwise, and the mixture is stirred at 40° C. for 24 hours. Thereafter, the reaction solution is neutralized with hydrobromic acid and filtered to obtain Cat-5. Note that methyl iodide is added to capture an anion species generated by abstracting hydrogen atoms from a phenol group of polyhydroxystyrene by a base.

[Chem. 12]

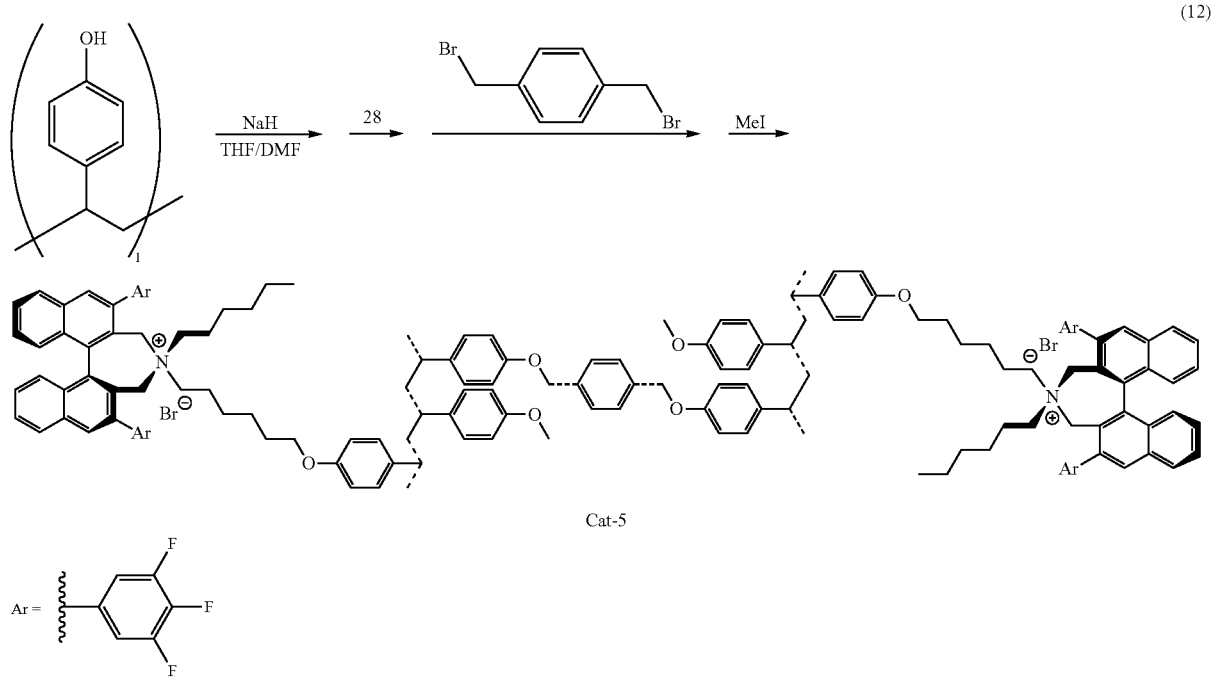

(12)

By using Compound 24, which is the spiro-type quaternary ammonium compound, as a raw material, Cat-6 can be obtained by the same method as the formula (12) (the following formula (13)).

[Chem. 13]

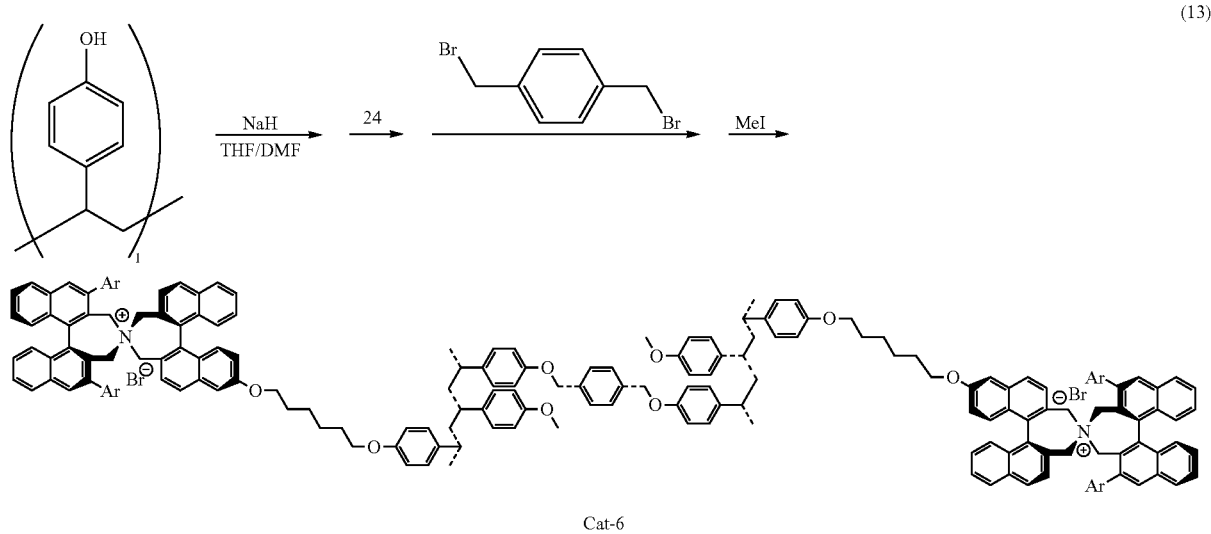

(13)

-continued

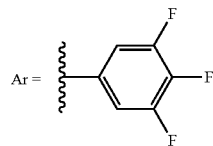

In the synthetic methods of the above formulas (12) and (13), instead of polyhydroxystyrene or in addition to polyhydroxystyrene, for example, a crosslinked polymer having a functional group such as a hydroxy group and an amino group in a side chain as illustrated in the following formula (14) may be used. In some cases, it may be unnecessary to add a crosslinking agent. In the following formula (14), P represents a polymer.

[Chem. 14]

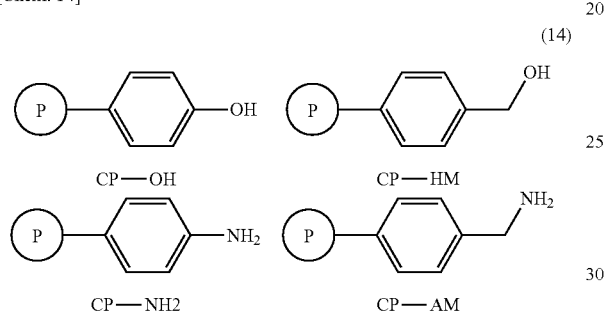

(14)

[Chem. 15]

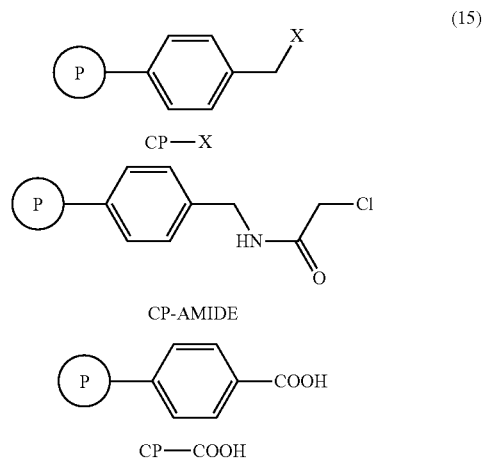

(15)

Examples of a polymer corresponding to P include: a polymer having an alkyl chain which may have a substituent or a side chain group; a polymer having an ether structure such as a polyoxyalkylene, where the ether structure has a carbon atom and an oxygen atom in the main chain, and may have a substituent or a side chain group; a polymer having a structure such as a polyethyleneimine, where the structure has a carbon atom and a nitrogen atom in the main chain and may have a substituent or a side chain group; a polymer having a structure such as a siloxane, where the structure has an atom of an element such as a silicon atom other than a carbon atom, an oxygen atom and a nitrogen atom in the main chain, and may have a substituent or a side chain group in the main chain; a polymer having a structure such as a nylon structure which may have a substituent or a side chain group, or a vinylon structure which may have a substituent or a side chain group; a polymer having a polyester structure such as polyethylene terephthalate, where the polyester structure may have a substituent or a side chain group; a polymer having a structure which may have a substituent or a side chain group, where the structure has a plurality of amide bonds in the main chain and may have a substituent; and a polymer having a polyimide structure which may have a substituent or a side chain group, or a polysaccharide structure which may have a substituent or a side chain group.

Compounds having a functional group such as hydroxy in the ammonium salt of the catalytic center as in Compounds 22 and 31 may bond to, for example, a polymer such as: CP-X, which is a halogenated benzyl type polymer having a highly active halogen atom-carbon atom bond; CP-AMIDE, which is a polymer having an amide group and a halogen atom at α-position of a carbonyl group; and CP—COOH, which is a polymer having a carboxyl group as a support. Note that P in the following formula (15) represents a polymer chain.

Examples of a polymer corresponding to P include: a polymer having an alkyl chain which may have a substituent or a side chain group; a polymer having an ether structure such as a polyoxyalkylene, where the ether structure has a carbon atom and an oxygen atom in the main chain, and may have a substituent or a side chain group; a polymer having a structure such as a polyethyleneimine, where the structure has a carbon atom and a nitrogen atom in the main chain and may have a substituent or a side chain group; a polymer having a structure such as a siloxane, where the structure has an atom of an element such as a silicon atom other than a carbon atom, an oxygen atom and a nitrogen atom in the main chain and may have a substituent or a side chain group in the main chain; a polymer having a structure such as a nylon structure which may have a substituent or a side chain group, or a vinylon structure which may have a substituent or a side chain group; a polymer having a polyester structure such as polyethylene terephthalate, where the polyester structure may have a substituent or a side chain group; a polymer having a structure which may have a substituent or a side chain group, where the structure has a plurality of amide bonds in the main chain and may have a substituent; and a polymer having a polyimide structure which may have a substituent or a side chain group, or a polysaccharide structure which may have a substituent or a side chain group.

When a steric hindrance of the catalyst center is large, it is preferred that a polymer as illustrated in the following formula (16) in which a number of bonds from a base main chain skeleton is 7 or more, the bonds including a bond between the polymer chain and a carbon atom in a benzene ring bonding to the polymer chain, is used as a support.

[Chem. 16]

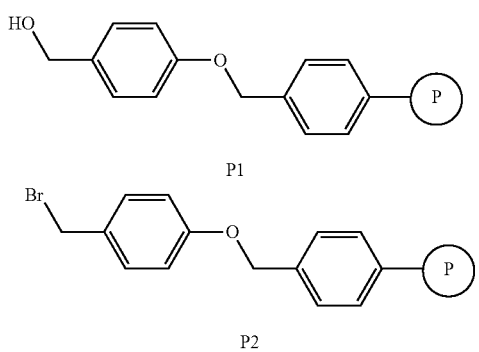

(16)

Further, instead of the polyhydroxystyrene in the synthetic methods of the above formulas (12) and (13), for example, a material having a functional group such as a hydroxy group and an amino group and being an inorganic material such as a silica and an alumina as a base material, as illustrated in the following formula (16), may be used. In this case, it may be unnecessary to add a crosslinking agent.

[Chem. 17]

(17)

Silica O—Si—CH₂CH₂CH₂—OH    Silica O—Si—CH₂CH₂CH₂—NH₂

SiO—OH                SiO—HM

A linker used for bonding from the organic polymer and the inorganic base material to the catalytic center may have, for example, an aryl group, an alkyl chain, an amide bond, an ether bond, a thioether bond, a disulfide bond, an imide bond, a single bond or a double bond between a carbon atom and a nitrogen atom, a bond between a phosphorus atom and a carbon atom, or a bond between a phosphorus atom and an oxygen atom. In particular, the linker having one or two kinds of bonds among a bond between carbon atoms, a bond between a carbon atom and an oxygen atom, and a bond between a carbon atom and a nitrogen atom is preferable because they are chemically stable.

For example, practically, the P1 and the chiral ammonium salt can be connected by a method illustrated in the following formula (18).

[Chem. 18]

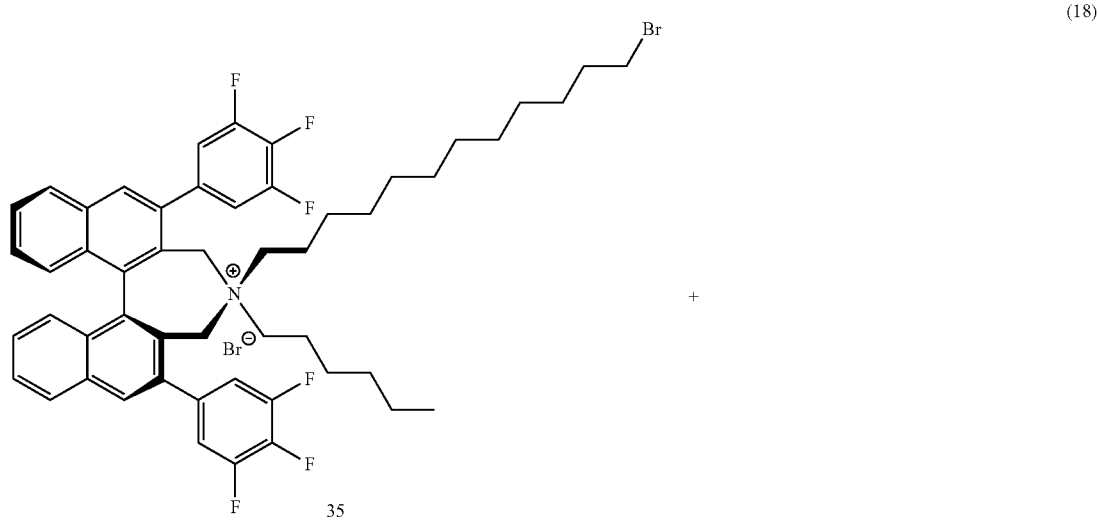

(18)

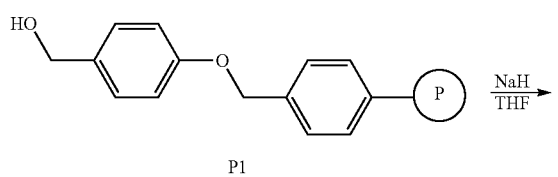

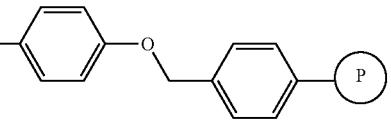

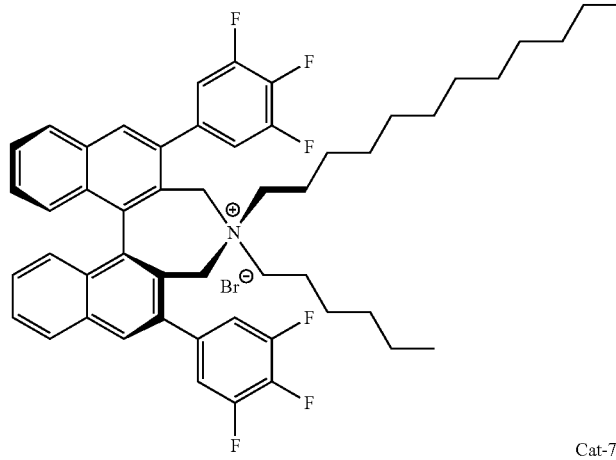

Cat-7

Polymer P1 (50-100 mesh, 1.0 mmol/g OH) illustrated in the above formula (16) is added to 18 mg of an oil in which sodium hydride is dispersed (content of sodium hydride: 40%) in tetrahydrofuran (THF) at room temperature, and stirred for 15 minutes. Then, a tetrahydrofuran solution of Compound 35 (48 mg; 0.05 mmol) is added at room temperature and stirred at 40° C. for 12 hours. Thereafter, the reaction solution is neutralized with hydrobromic acid and filtered to obtain Cat-7. Cat-7 includes a linker composed of 24 constituent atoms and the linker includes a hydrocarbon group in which 12 carbon atoms are connected. When it is necessary to weaken an interaction between the polymer chain and the catalyst center or the cation center to obtain higher stereoselectivity in an asymmetric reaction, the number of constituent atoms of the linker is preferably 24 or more, more preferably 30 or more, further preferably 40 or more.

Compound 35, in which chain lengths of the two substituents on the nitrogen atom of the cation center are different from each other, is synthesized by the same method as the method for synthesizing Compound 28 from Compound 21 of the above formula (7).

Cat-8, illustrated in the following formula (19), is also obtained by using CP-AMIDE. Specifically, a polymer CP-AMIDE (50-100 mesh, 1.0 mmol/g OH) represented by the above formula (15) is added to 18 mg of an oil in which sodium hydride is dispersed (sodium hydride content: 40% 1.0 mmol/gOH) in tetrahydrofuran (THF) at room temperature and the mixture is stirred for 15 minutes. Then, a tetrahydrofuran solution of Compound 35 (48 mg; 0.05 mmol) is added at room temperature and stirred at 40° C. for 12 hours. Thereafter, the reaction solution is neutralized with hydrobromic acid and filtered to obtain Cat-8.

[Chem. 19]

(19)

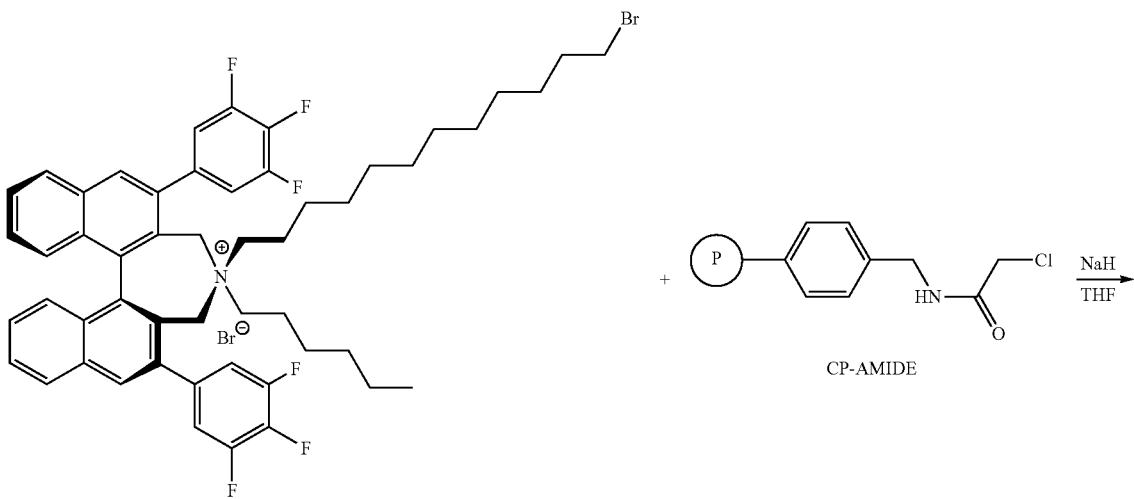

35            CP-AMIDE

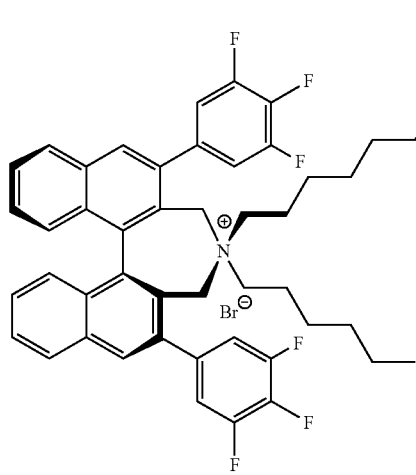

Cat-8

By making the chain lengths of two substituents on the nitrogen atom of the cation center different from each other like Compound 35, a steric hindrance at the chiral center may be decreased, so that it may facilitate to bond to the polymer.

Also when the nitrogen atom of the cation center has a cyclic structure containing the nitrogen atom like the compound 36, the steric hindrance of the chiral center may be decreased, so that it may become easier to bond to the polymer. As illustrated in the following formula (20), 2 equivalents of 4-piperidine ethanol and 2.5 equivalents of potassium carbonate based on Compound 21 are added and the mixture is heated to reflux with stirring for 48 hours to obtain Compound 36 in 80% yield.

Compound 36 can bond to the polymer in the method described above.

A compound such as compound 37 which is not an axially chiral type chiral compound can also bond to a polymer. P2 (100-200 mesh, 1.0 mmol/g Br) illustrated in the above formula (16) is added to 18 mg of an oil in which sodium hydride is dispersed (content of sodium hydride: 40%) in tetrahydrofuran at room temperature. Then Compound 37 (50 mg; 0.05 mmol) is added and stirred at 40° C. for 12 hours. Thereafter, the reaction solution is neutralized with hydrobromic acid and filtered to obtain Cat-9. Note that Compound 37 can be obtained by the methods described in *Syn Commun.*, 2010, 40, 266. and *J. Am. Chem. Soc.*, 2003, 125, 11206. as references.

[Chem. 20]

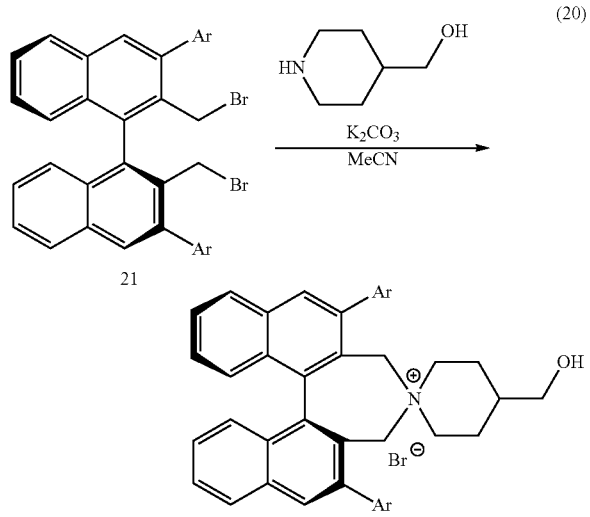

[Chem. 21]

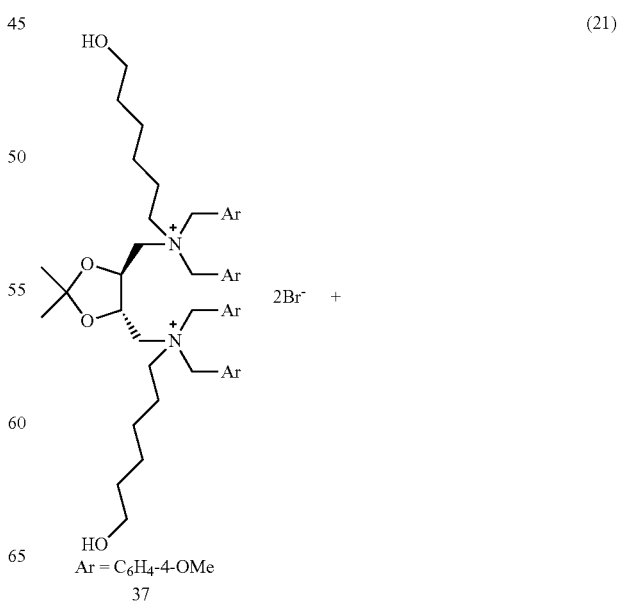

Ar = $C_6H_4$-4-OMe

37

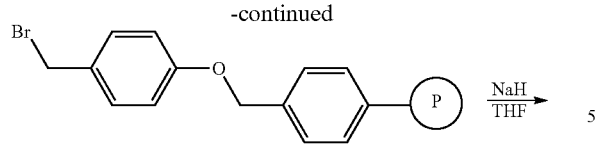
$\xrightarrow{\text{NaH}}{\text{THF}}$
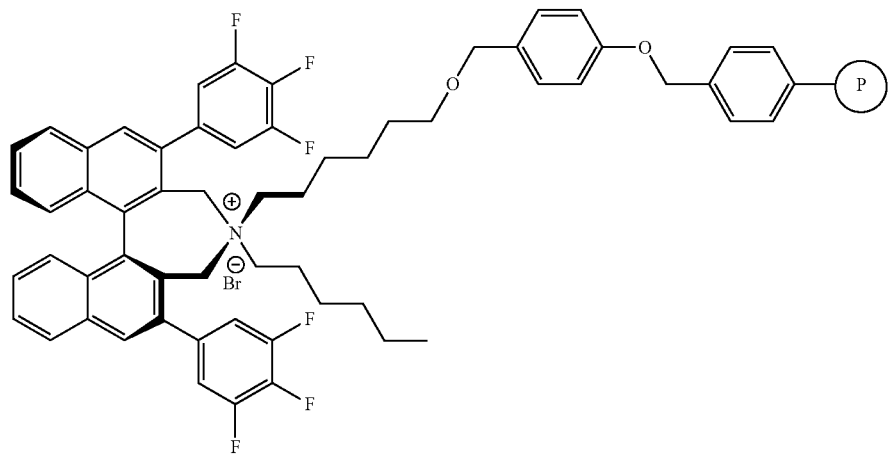
Cat-10 to Cat-13 illustrated in the following formula (22) can be synthesized by using P1 or P2.
[Chem. 22]
(22)
Cat-10

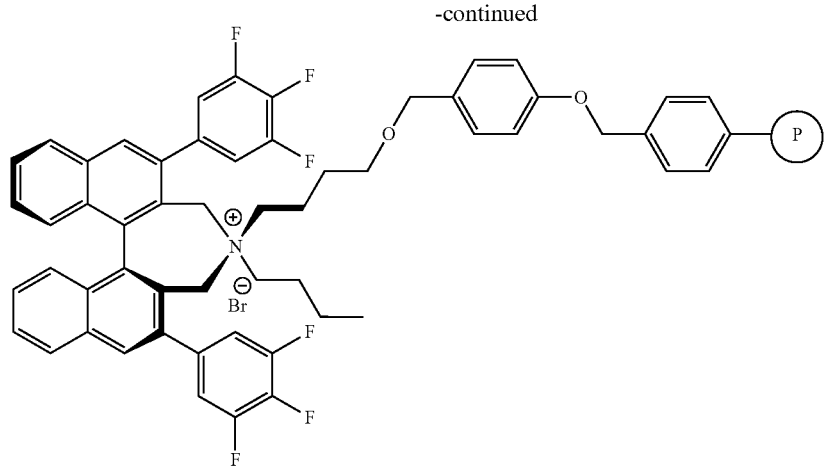
Cat-11
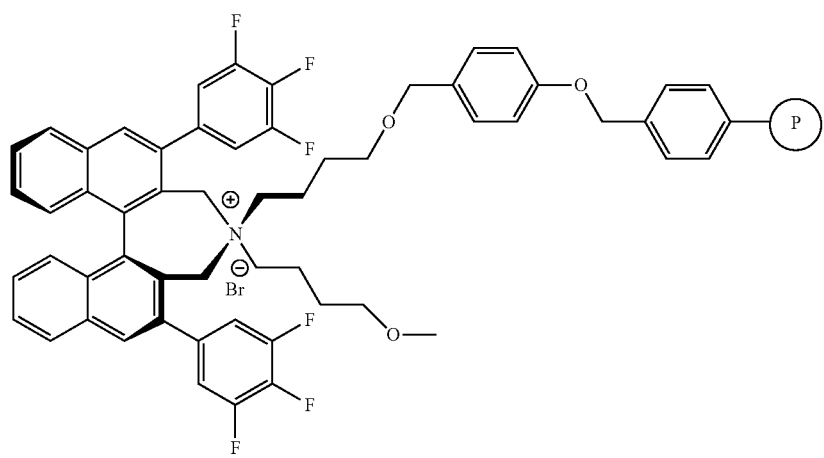
Cat-12
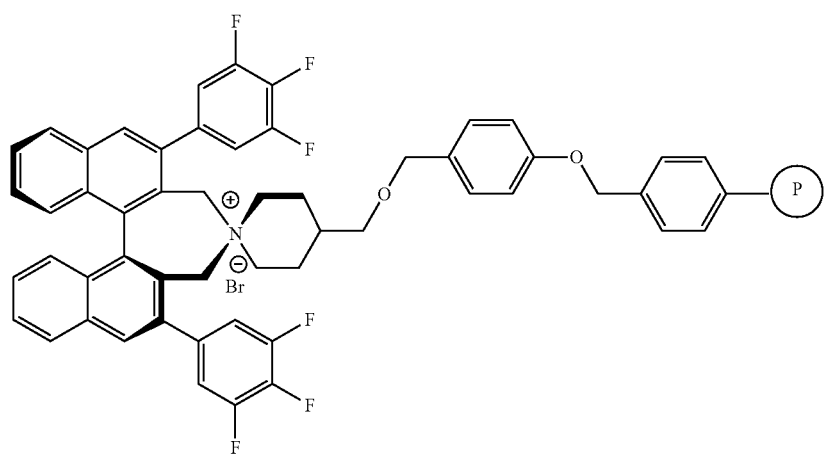
Cat-13

Figure 11:
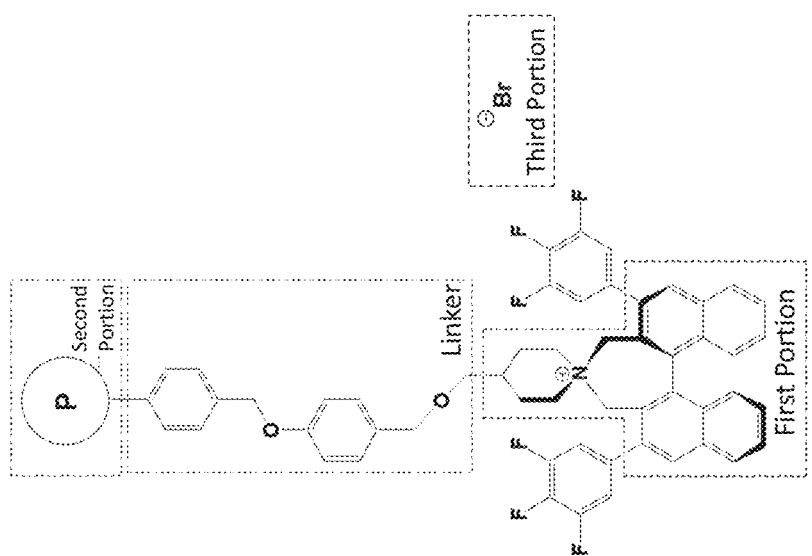
FIG. 11 illustrates a typical compound according to one embodiment of the present invention.

FIG. 11 illustrates sections of the first portion, the second portion, the third portion and the linker in Cat-13. A portion including: a binaphthyl group being the axially chiral substituent; a seven-membered ring composed of a plurality of atoms of constituent atoms contained in the binaphthyl group skeleton, a carbon atom at 2-position of the binaphthyl group, a carbon atom at 2'-position of the binaphthyl group, a methylene group bonding directly to 2-position of the binaphthyl group, a methylene group bonding directly to 2'-position of the binaphthyl group and a nitrogen atom bonding directly to the two methylene groups; and a six-membered ring including the nitrogen atom is defined as the first portion. This is because, similar to the compound exemplified in FIG. 6, a conformational movement of the seven-membered ring and the six-membered ring is substantially restricted by a steric effect of the binaphthyl group which is the axially chiral substituent. Two trifluorophenyl groups bonding to a carbon atom at 3-position and a carbon atom at 3'-position of the binaphthyl group skeleton are not included in the first portion, since bonds between the trifluorophenyl groups and each of the carbon atoms at 3- and 3'-positions are rotatable.

The linker includes a portion from a methylene group bonding directly to a carbon atom being opposite to the nitrogen atom contained in the six-membered ring to a carbon atom of a benzene ring bonding directly to a polymer chain P. The second portion and the third portion is the polymer chain P being a base and a bromide ion, respectively.

Cat-14 to Cat-17 illustrated in the following formula (23) can be synthesized by using P-AMIDE.

[Chem. 23]

(23)

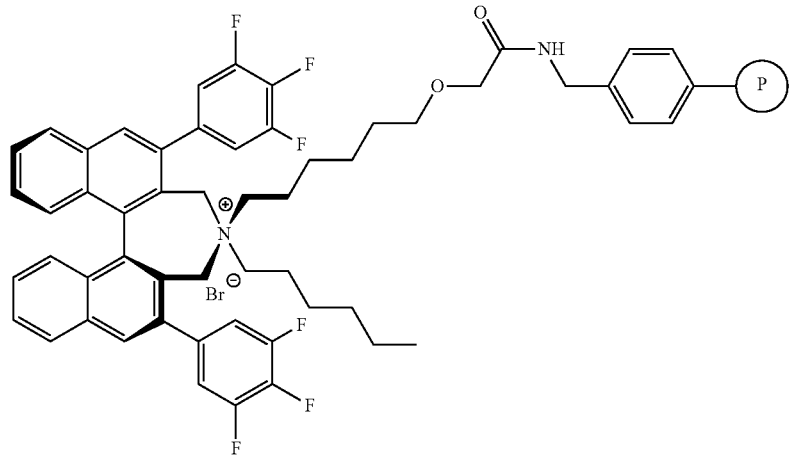

Cat-14

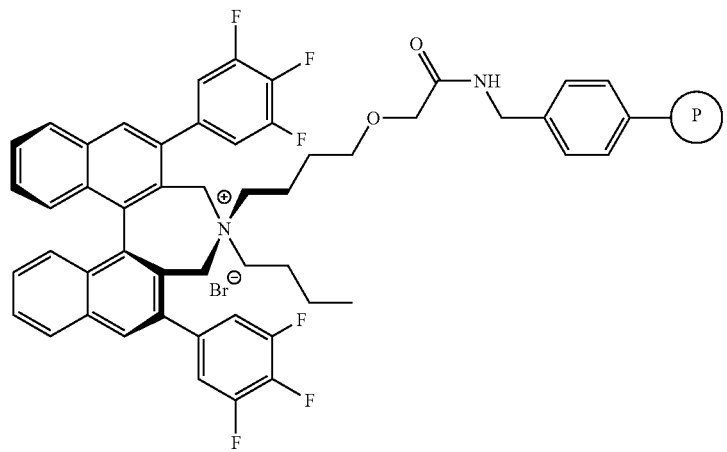

Cat-15

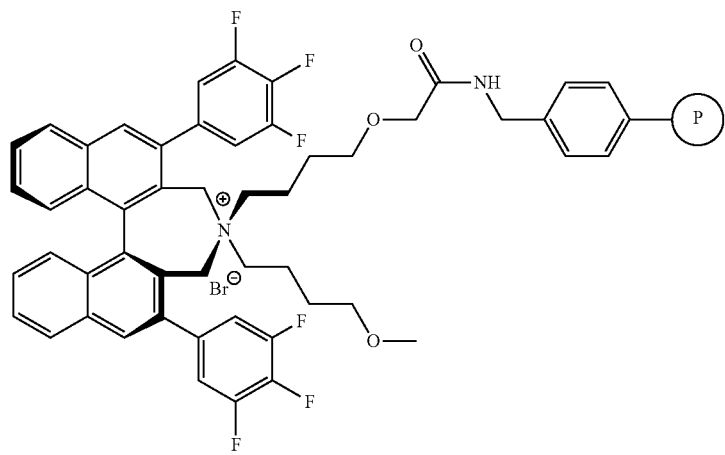
Cat-16
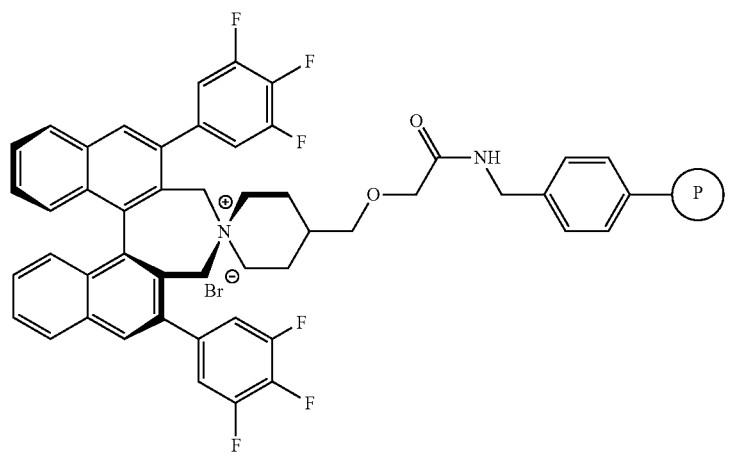
Cat-17

Cat-12 and Cat-16 have a substituent having a methoxy group, which has an oxygen atom of less coordinating ability at an end, on the nitrogen atom which is the cation center as a substituent which is not the linker.

In any one of the above compounds, when the compound is an organic salt, a compound illustrated in the following formula (24) can be synthesized to investigate an effect by the structure in which a coordinating nitrogen atom is present within 6 bonds counted from a bond having an atom which is a cation or an anion center.

[Chem. 24]

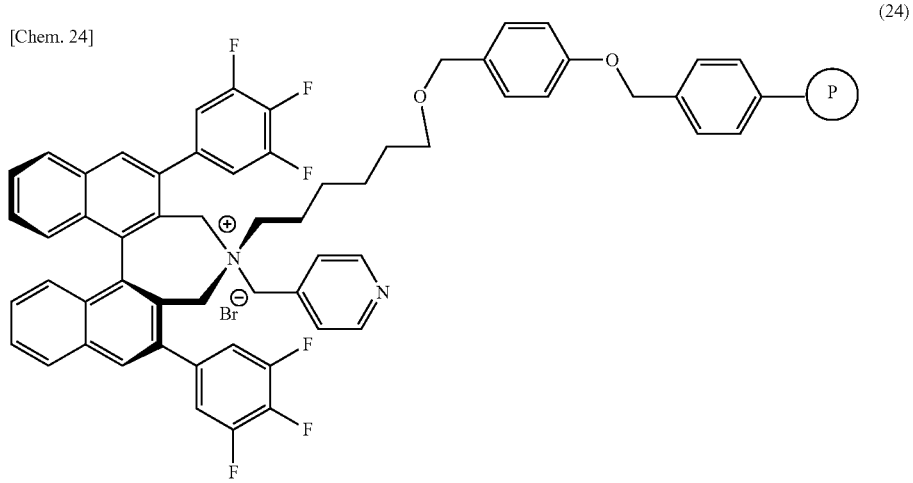

(24)

Cat-18

Cat-18 may be synthesized in the same method as the synthesis of Compound 28 illustrated in the above formula (7). Specifically, a compound is reacted with 4-(bromomethyl) pyridine instead of hexyl bromide and then connected with P-1 by the same method as in the above formula (18).

Cat-18 has a coordinating nitrogen atom in a pyridine skeleton in the fifth bond counted from a bond having a nitrogen atom which is the cation center.

The Cat-3, Cat-4, and Cat-5 are catalysts including an alkylene group in a portion constituting an organic group connecting nitrogen atom of the cation center of the ammonium salt with the polymer chain, the alkylene group bonding directly to the nitrogen atom, bonding to an oxygen atom on a phenyl group of a polystyrene, and composed of 6 carbon atoms. And another alkyl group on the nitrogen group also constituted by bonding of 6 carbon atoms. That is, the catalysts may have alkyl groups of the same chain length on the nitrogen atom which is the cation center of the ammonium salt.

However, other than the two substituents between the binaphthyl group on the nitrogen atom which is the cation center of the ammonium salt, depending on an application of a reaction to be catalyzed, a desired reactivity or reaction mode, the number of constituent atoms of the substituent on the nitrogen atom may be made different like Cat-7 and Cat-8.

In order to reduce an interaction between the portion of the ammonium salt which is the catalytic center and the polymer chain or resin which is a support, it is preferred that the chain length of the organic group bonding the nitrogen atom and the polymer chain is set so that a cyclic structure including the binaphthyl group and the nitrogen atom is not influenced. Specifically, the linker connecting the polymer chain with the nitrogen atom preferably may have a substituent or a structure which is to be four or more bonds from the nitrogen atom which is the cation center.

An organic reaction is carried out using the above-mentioned Cat-1 to Cat-18 as a solid catalyst, and its optical yield is examined.

The following formula (25) describes an application example for a carbon-carbon bond reaction as a specific example. The reaction represented by the following formula (25) is a reaction of a Schiff base and an alkyl halide having an alkyl group which may have a substituent such as an aryl group in the presence of a base. By this reaction, an alkyl group bonds to α-position of an ester group.

[Chem. 25]

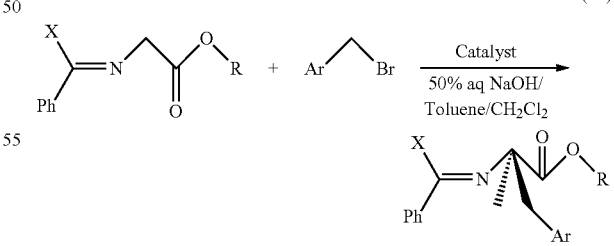

(25)

Specific reaction conditions are as follows: N-(diphenylmethylene)glycine tert-butyl ester (0.065 g; 0.22 mmol) and benzyl bromide (0.375 g; 2.2 mmol) are dissolved in a mixed solvent of toluene/dichloromethane (=7/3, volume ratio), 1 mmol % of the above-mentioned compounds Cat-1 to 18 as a solid-molecular catalyst is added, and 50% aqueous sodium hydroxide solution (0.55 mL) is further added. The mixture is stirred at room temperature for 16 hours and the reaction product is analyzed. A chemical yield is determined by isolating the reaction product and an optical yield is measured by liquid phase chromatography equipped with a chiral column for analysis.

TABLE 1

Yields, optical yields and catalyst recovery rates in batch reactions in a 50% NaOH aqueous solution-toluene/methylene chloride solvent system (two-phase system) by using catalysts according to some embodiments of the invention

| Catalyst | Yield/% | Optical Yield/% ee | Catalyst Recovery Rate/% |
|---|---|---|---|
| Cat-1 | 75 | 70 | 70 |
| Cat-2 | 80 | 73 | 90 |
| Cat-3 | 80 | 72 | 70 |
| Cat-4 | 80 | 72 | 90 |
| Cat-5 | 80 | 72 | 90 |
| Cat-6 | 83 | 78 | 93 |
| Cat-7 | 70 | 68 | 78 |
| Cat-8 | 70 | 68 | 75 |
| Cat-9 | 68 | 68 | 72 |
| Cat-10 | 74 | 65 | 72 |
| Cat-11 | 72 | 70 | 72 |
| Cat-12 | 70 | 68 | 70 |
| Cat-13 | 70 | 69 | 72 |
| Cat-14 | 74 | 68 | 73 |
| Cat-15 | 70 | 65 | 70 |
| Cat-16 | 70 | 62 | 72 |
| Cat-17 | 68 | 70 | 72 |
| Cat-18 | 58 | 35 | 70 |

As can be seen from Table 1, when Cat-1 to Cat-17 are used as the solid chiral molecular catalyst, the catalysts give good yields and optical yields. On the other hand, when Cat-18 in which a coordination nitrogen atom is present in the fifth bond counted from a bond containing a nitrogen atom, which is a cation center, is used as a catalyst, it is observed that the yield and optical yield are low.

At least 70% or more of the catalyst can be recovered by an operation such as filtration of the reaction solution after the reaction using Cat-1 to Cat-18 as a catalyst, and the recovered catalyst can be reused. Therefore, it is possible to reuse an asymmetric catalyst which is extremely expensive as a homogeneous catalyst due to an expensive raw material and many synthetic steps.

Particularly, with respect to Cat-2, Cat-4, Cat-5 and Cat-6 having a crosslinked structure, the catalyst recovery rate of 90% or more is observed. It is indicated that the insolubility is improved by forming a crosslinked structure at the time of synthesizing the compound.

Next, yields, optical yields and catalyst recovery rates in a batch reaction in a 50% KOH aqueous solution-toluene solvent system by using Cat-1 to Cat-18 as a catalyst are described.

TABLE 2

Yields, optical yields and catalyst recovery rates in batch reactions in a 50% KOH aqueous solution-toluene solvent system (two-phase system) by using catalysts according to some embodiments of the invention

| Catalyst | Yield/% | Optical Yield/% ee | Catalyst Recovery Rate/% |
|---|---|---|---|
| Cat-1 | 75 | 80 | 75 |
| Cat-2 | 80 | 80 | 94 |
| Cat-3 | 80 | 75 | 74 |
| Cat-4 | 80 | 75 | 94 |
| Cat-5 | 80 | 85 | 95 |
| Cat-6 | 83 | 86 | 97 |
| Cat-7 | 70 | 71 | 80 |
| Cat-8 | 70 | 73 | 78 |
| Cat-9 | 73 | 72 | 80 |
| Cat-10 | 74 | 75 | 80 |
| Cat-11 | 72 | 72 | 75 |
| Cat-12 | 70 | 70 | 74 |
| Cat-13 | 70 | 72 | 75 |
| Cat-14 | 74 | 72 | 77 |
| Cat-15 | 70 | 70 | 73 |
| Cat-16 | 70 | 65 | 75 |
| Cat-17 | 68 | 72 | 74 |
| Cat-18 | 58 | 48 | 76 |

As can be seen from Table 2, the optical yields are higher in the 50% KOH aqueous solution-toluene solvent system as a whole. It is considered that due to a high polarity of methylene chloride, methylene chloride slightly dissolves in water, so that reactions occur at a field other than the asymmetric reaction field formed by Cat-1 to Cat-18.

Since Cat-1, Cat-2, Cat-3, Cat-4, Cat-5, Cat-6, Cat-7 and Cat-8 have highly insolubility, they can be used as a catalyst of a flow reaction by filling them into a column. Unlike the batch reaction described above, the flow reaction has an advantage that the catalyst can be used repeatedly without recovering by the operation such as filtration.

Figure 1:
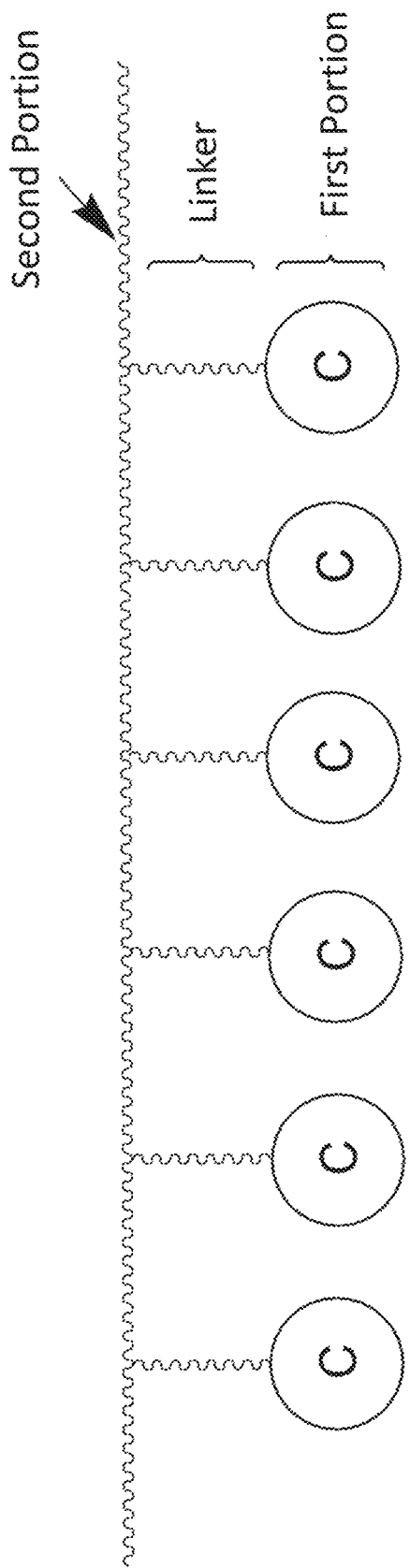
FIG. 1 illustrates a typical schematic structure of a compound according to an embodiment of the present invention.
Figure 2:
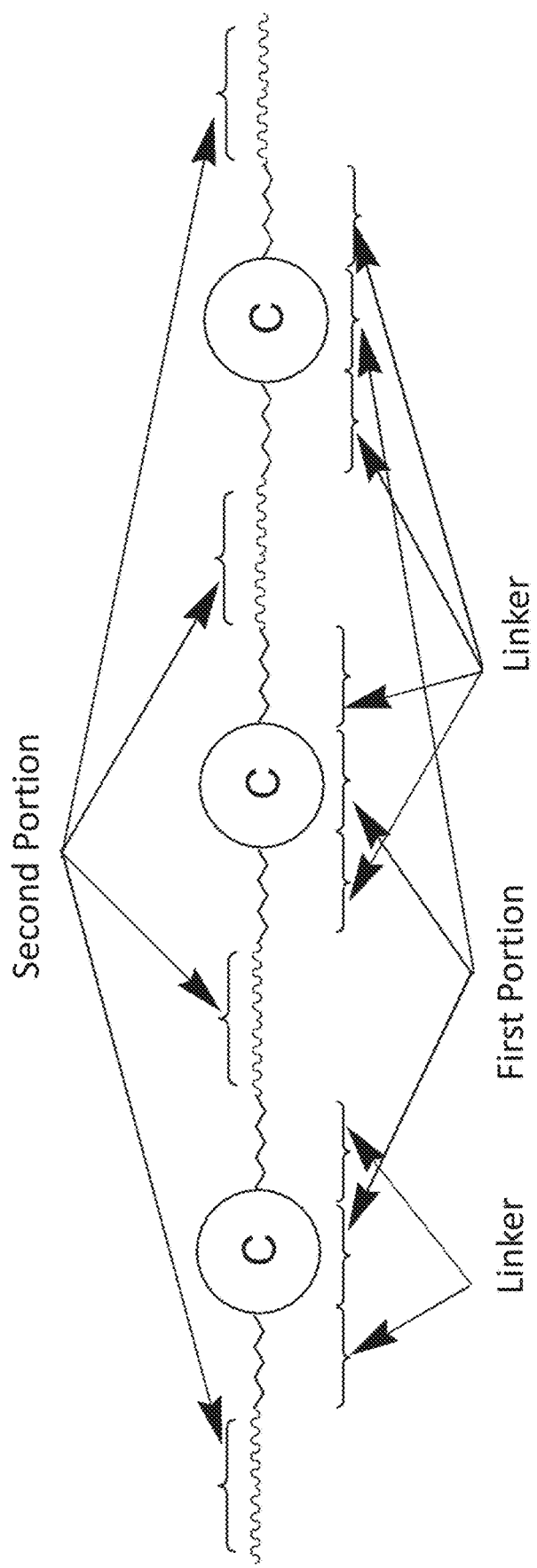
FIG. 2 illustrates a typical schematic structure of a compound according to another embodiment of the present invention.
Figure 3:
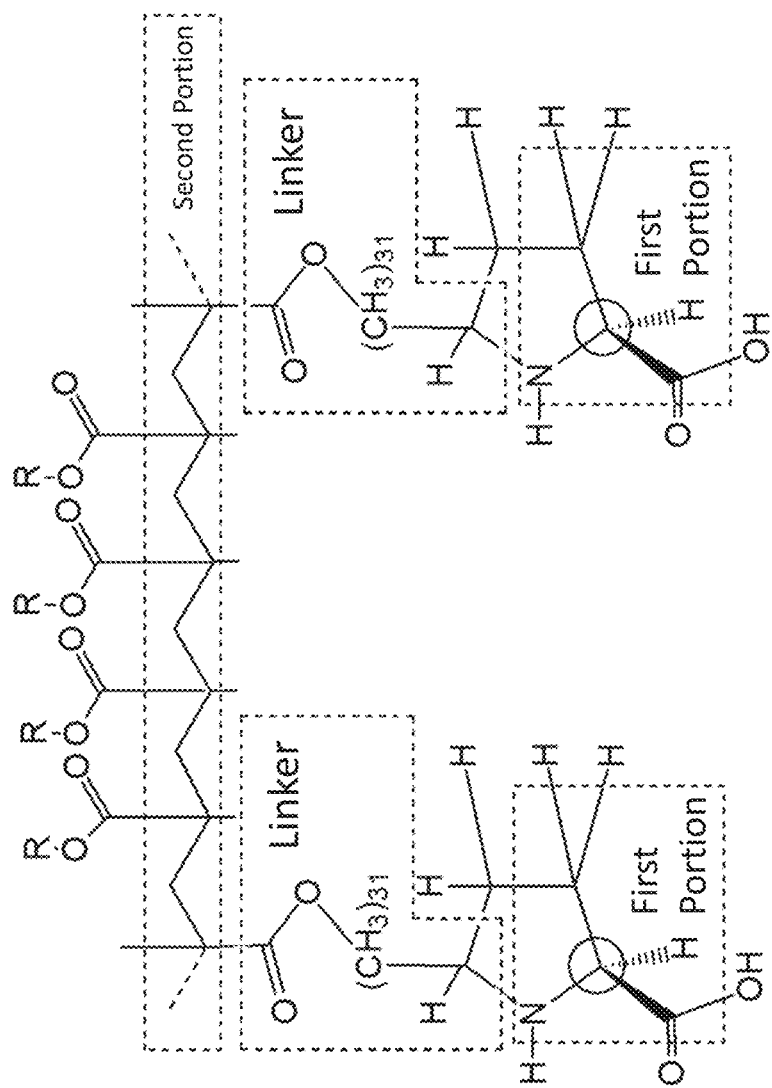
FIG. 3 illustrates a typical compound according to one embodiment of the present invention.
Figure 4:
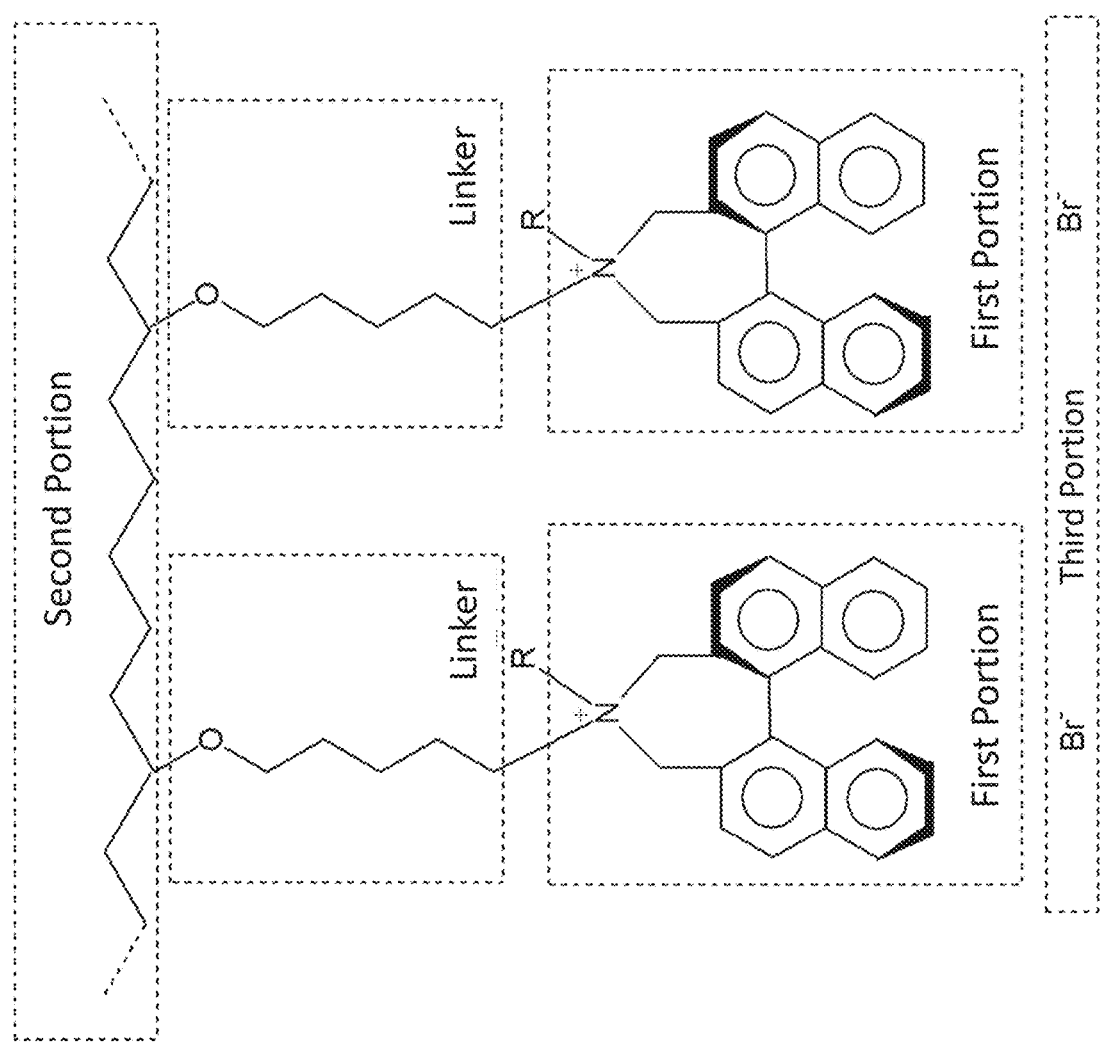
FIG. 4 illustrates a typical compound according to one embodiment of the present invention.
Figure 5:
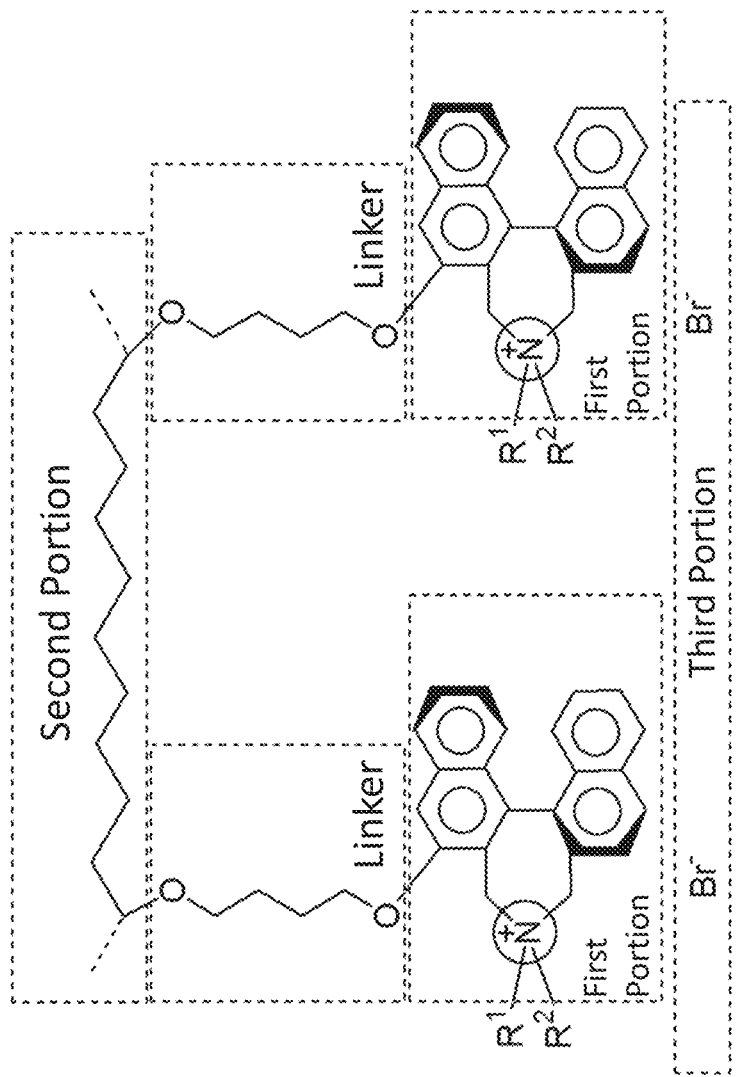
FIG. 5 illustrates a typical compound according to one embodiment of the present invention.
Figure 12:
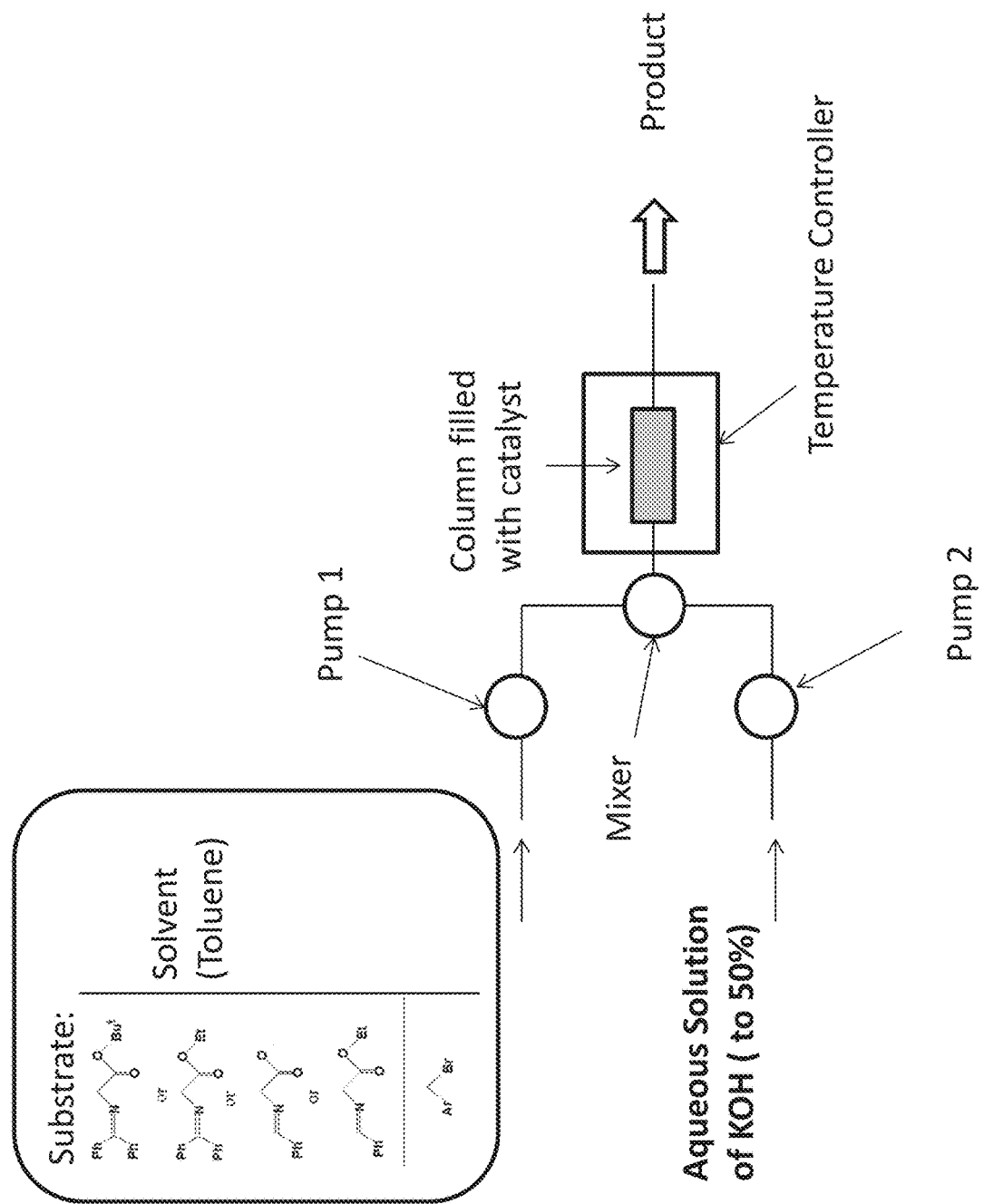
FIG. 12 illustrates a schematic diagram of a flow reaction.

FIG. 12 illustrates a schematic diagram of the flow reaction. As illustrated in FIG. 2, by mixing two solutions via a T-shaped or Y-shaped mixer, even when incompatible reaction solvents such as toluene and potassium hydroxide aqueous solution, sodium hydroxide aqueous solution or the like are used, the reaction solvent can be smoothly introduced into the column.

As a substrate, a benzylideneamino ester or a benzhydrylideneamino ester as illustrated in FIG. 12 can be used, and Table 3 describes the case where the same reaction system as the reaction system illustrated in Table 2 is adopted.

TABLE 3

Yields and optical yields in flow reactions using catalysts according to some embodiments of the present invention

| Catalyst | Yield/% | Optical Yield/% ee |
|---|---|---|
| Cat-1 | 89 | 76 |
| Cat-2 | 86 | 75 |
| Cat-3 | 87 | 70 |
| Cat-4 | 87 | 70 |
| Cat-5 | 86 | 80 |
| Cat-6 | 89 | 82 |
| Cat-7 | 80 | 70 |
| Cat-8 | 78 | 68 |

As can be seen from Table 3, good yields and optical yields can be obtained by applying any catalyst to the flow reaction system. Even when any one of Cat-1 to Cat-8 is used as a catalyst, it can be repeatedly used for the reaction at least five times or more.

As the chiral center of the compound according to some embodiments of the present invention, compounds represented by the following formula (26) can be used. The substituents R may be the same or different from each other, and the position of substitution can be appropriately set.

[Chem. 26]

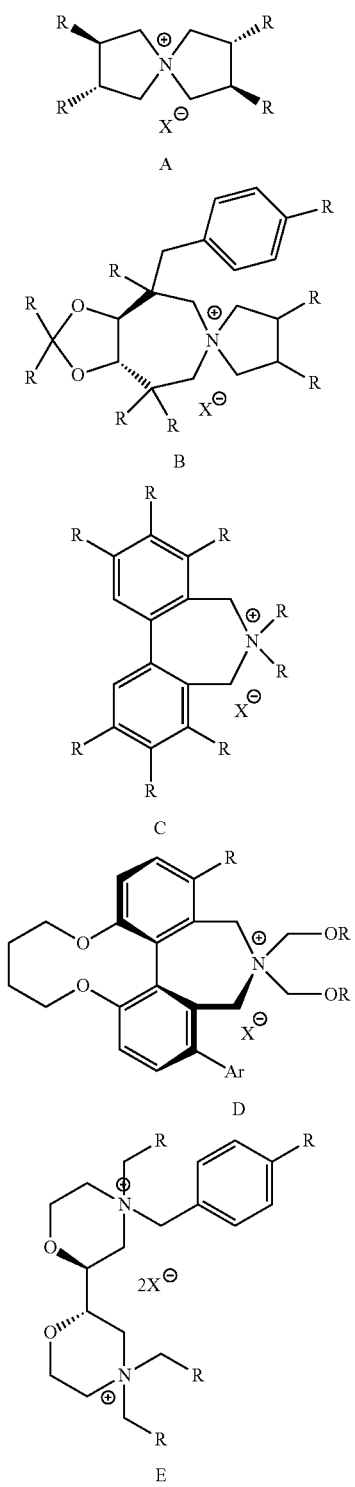

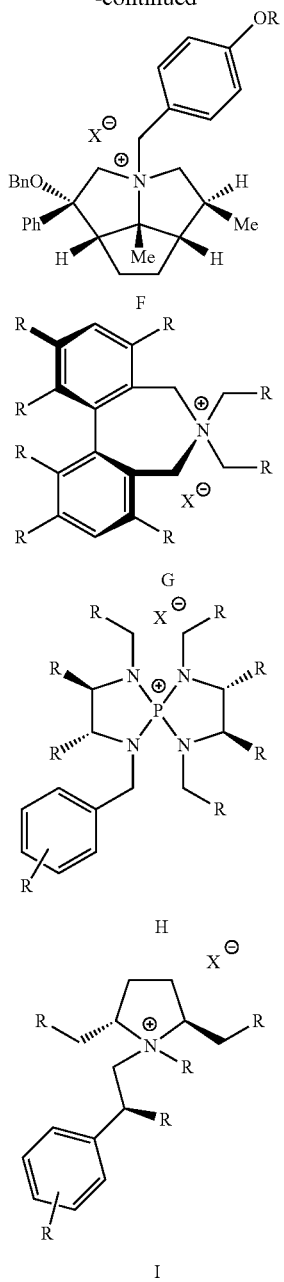

Specifically, a compound having a Spiro structure such as A and B, a compound having an axially chiral biphenyl skeleton such as C, D and G, a compound having a polycyclic structure sharing at least one side such as F, and a compound in which a hetero atom such as a phosphorus atom other than a nitrogen atom is the cation center such as H can be applied.

Similar to the compound having the binaphthyl skeleton described above, the above-mentioned compounds A to I can also bond to the polymer chain by using the substituent R appropriately.

Similar to other compounds of the present invention, the above-mentioned A to I skeletons may bond to the polymer chain through an alkyl chain, a polyether chain, a triazole structure, an amide group, a thioamide group, an ester group, a thioester group, a carbamate group, an amine structure, a sulfide structure, a disulfide structure, an ether structure or the like.

Each of the constituent parts of the compound according to the present invention, such as the chiral center or cation center, the polymer chain, and the linker connecting the chiral center or the cation center with the polymer chain can be appropriately selected, and combinations thereof are also appropriately selected, unless it is going against the gist of the present invention.

The invention claimed is:

1. A compound comprising:
    a plurality of first portions;
    a second portion;
    a third portion; and
    a linker that connects each of the plurality of first portions with the second portion and that has at least one covalent bond,
    wherein each of the plurality of first portions has a chirality;
    the chirality is induced by any one selected from the group consisting of an axial chirality, a planar chirality and a helix;
    when the chirality is induced by an axial chirality,
        each of the plurality of first portions has an axially chiral substituent to be the axial chirality,
        the linker bonds directly to: a second atom contained in a cyclic structure that shares a plurality of atoms in constituent atoms that constitute the axially chiral substituent; or a third atom contained in the axially chiral substituent, and
        a bond between: a fourth atom; and the second atom or the third atom is rotatable, the fourth atom being contained in the linker and bonding directly to the second atom or the third atom;
    when the chirality is induced by a planar chirality,
        the compound has a planar-chiral substituent to be the planar chirality,
        the linker bonds directly to a fifth atom contained in the planar-chiral substituent, and
        a bond between a sixth atom and the fifth atom is rotatable, the sixth atom being contained in the linker and bonding directly to the planar-chiral substituent;
    when the chirality is induced by a helix,
        the compound has a helical substituent to be the helix,
        the linker bonds directly to a seventh atom contained in the helical substituent, and
        a bond between an eighth atom and the seventh atom is rotatable, the eighth atom bonding directly to the helical substituent;
    the compound is an organic salt including a cation portion and an anion portion;
    the anion portion is the third portion; and
    the cation portion includes the plurality of first portions, the second portion and the linker.

2. The compound of claim 1, wherein the axially chiral substituent, the planar-chiral substituent and the helical substituent have no freely rotatable bond.

3. The compound of claim 1, wherein each of the plurality of first portions has the axially chiral substituent.

4. The compound of claim 1, wherein each of the plurality of first portions has a binaphthyl group that induces the chirality and a nitrogen atom; and
    one part of the binaphthyl group and the nitrogen atom constitute at least one part of a cyclic structure.

5. The compound of claim 4, wherein the nitrogen atom bonds to a carbon atom at 2-position of the binaphthyl group and a carbon atom at 2'-position of the binaphthyl group through a first methylene group and a second methylene group, respectively;
    the nitrogen atom further bonds to a first organic group and a second organic group other than the first methylene group and the second methylene group; and
    the linker has the first organic group.

6. The compound of claim 1, wherein each of the plurality of first portions has a cationic center of an ammonium salt.

7. The compound of claim 1, wherein the second portion constitutes a main chain of a polymer.

8. The compound of claim 7, wherein a constituent atom in the main chain of the polymer is a carbon atom.

9. The compound of claim 1, wherein the linker has a hydrocarbon group having 6 or more carbon atoms.

10. The compound of claim 1, wherein the linker has an aryl group; and
    the aryl group bonds to the second portion.

11. The compound of claim 1, wherein the second portion has a branched or crosslinked structure.

12. The compound of claim 1, wherein the compound is a catalyst that induces a chirality.

13. The compound of claim 1, wherein the axially chiral substituent has an allenyl group, biphenyl group or a binaphthyl group which may have a substituent;
    the planar-chiral substituent has a cyclophane structure, a trans-cyclooctene or a ferrocenyl structure which may have a substituent; and
    the helical substituent has a helical structure in which a plurality of aromatic rings or heterocyclic rings bond.

14. A method for manufacturing an organic material comprising:
    a first step of proceeding with an organic reaction by using the compound of claim 1 as a catalyst.

15. The method of claim 14, further comprising:
    a second step of recovering the compound after the first step.

16. The method of claim 15, further comprising:
    a third step of reusing the recovered compound in the second step as a catalyst to proceed with an organic reaction.

17. A method for manufacturing an organic material comprising:
    a first step of preparing a container or a column filled with the compound according to claim 1; and
    a second step of proceeding with an organic reaction that uses the compound as a catalyst in the container or the column,
    wherein in the second step, a reaction reagent or a solution of the reaction reagent for the organic reaction is introduced into a first end of the container or the column and discharged from a second end that is an opposite end of the first end.

* * * * *